(12) United States Patent
Washizu et al.

(10) Patent No.: US 7,202,954 B2
(45) Date of Patent: Apr. 10, 2007

(54) TARGET DETECTING APPARATUS, TARGET DETECTION METHOD AND TARGET DETECTION SUBSTRATE

(75) Inventors: Shintaro Washizu, Shizuoka (JP); Yuki Matsunami, Shizuoka (JP); Takatoshi Kinoshita, Aichi (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 175 days.

(21) Appl. No.: 10/733,450

(22) Filed: Dec. 12, 2003

(65) Prior Publication Data

US 2004/0156749 A1    Aug. 12, 2004

(30) Foreign Application Priority Data

Dec. 13, 2002    (JP)    ............................. 2002-362706

(51) Int. Cl.
   *G01J 3/45*    (2006.01)
(52) U.S. Cl. .................. 356/451; 356/504; 356/632
(58) Field of Classification Search ........... 356/504, 356/451, 503, 630, 632, 73; 250/559.27, 250/559.28
   See application file for complete search history.

(56) References Cited

U.S. PATENT DOCUMENTS

| | | |
|---|---|---|
| 3,979,184 A | 9/1976 | Giaever |
| 3,985,617 A | 10/1976 | Yugari et al. |
| 4,350,761 A | 9/1982 | Yamamoto ............... 435/7.93 |
| 4,592,980 A | 6/1986 | Tomida et al. ............ 430/59.1 |
| 4,796,981 A | 1/1989 | Nishimura et al. ......... 359/289 |
| 4,810,639 A | 3/1989 | Pankratz .................. 435/7.4 |
| 4,819,239 A | 4/1989 | Sharp et al. ............... 327/12 |
| 4,828,917 A | 5/1989 | Wegner et al. ............. 428/333 |
| 4,868,105 A | 9/1989 | Urdea .......................... 435/6 |

(Continued)

FOREIGN PATENT DOCUMENTS

EP    1 288 662 A1    3/2003

(Continued)

OTHER PUBLICATIONS

Thomas M. Cooper, et. Al., "Formation of Polypeptide-Dye Multilayers by an Electrostatic Self-Assembly Technique," LANGMUIR 1995, vol. 11, No. 7, pp. 2713-2718.

(Continued)

*Primary Examiner*—Gregory J. Toatley, Jr.
*Assistant Examiner*—Marissa J. Detschel
(74) *Attorney, Agent, or Firm*—Sughrue Mion, PLLC

(57) ABSTRACT

A target detection apparatus is provided which can detect and quantitatively measure various detection targets such as pathogens. For this purpose, the apparatus comprises an optical irradiation unit which irradiates light; an optical interference unit which can interact with the detection target, interferes with the light irradiated from the optical irradiation unit and radiates it as interference light and change the wavelength of the interference light after interaction with the detection target; and an wavelength change detecting unit which detects the wavelength change of the interference light radiated by the optical interference unit. The wavelength change detecting unit preferably measures spectrums before and after wavelength change of the interference light, and their differential spectrum. Also provided is a target detection substrate comprising a film-like material on a substrate which, when interacting with a detection target, changes the wavelength of the interference light.

43 Claims, 21 Drawing Sheets

U.S. PATENT DOCUMENTS

| | | | |
|---|---|---|---|
| 4,909,990 A | 3/1990 | Block et al. | 422/82.11 |
| 4,933,285 A | 6/1990 | Patton | |
| 5,063,417 A | 11/1991 | Hopfield | |
| 5,138,026 A | 8/1992 | Miyasaka et al. | |
| 5,246,748 A | 9/1993 | Gillberg-Laforce et al. | 428/1.2 |
| 5,281,539 A | 1/1994 | Schramm | 204/403.11 |
| 5,304,631 A | 4/1994 | Stewart et al. | |
| 5,354,654 A | 10/1994 | Ligler et al. | 435/5 |
| 5,364,851 A | 11/1994 | Joran | |
| 5,756,296 A | 5/1998 | Cubicciotti | |
| 5,759,447 A | 6/1998 | Efron et al. | 252/582 |
| 5,766,784 A | 6/1998 | Baskaran et al. | 428/702 |
| 5,783,392 A | 7/1998 | Seibl et al. | 435/6 |
| 5,800,994 A | 9/1998 | Martinelli | 435/6 |
| 6,083,689 A | 7/2000 | Martinelli et al. | 435/6 |
| 6,087,100 A | 7/2000 | Meade et al. | |
| 6,096,273 A | 8/2000 | Kayyem et al. | |
| 6,124,963 A | 9/2000 | Schumaker | 359/245 |
| 6,238,864 B1 | 5/2001 | Yan | 435/6 |
| 6,248,539 B1 | 6/2001 | Ghadiri et al. | |
| 5,883,875 A1 | 7/2001 | Aiyer | |
| 6,261,152 B1 | 7/2001 | Aiyer | |
| 6,306,584 B1 | 10/2001 | Bamdad | |
| 6,392,756 B1 * | 5/2002 | Li et al. | 356/632 |
| 6,400,489 B1 | 6/2002 | Suzuki et al. | 359/241 |
| 6,451,543 B1 | 9/2002 | Kochendoerfer et al. | 435/7.1 |
| 6,686,150 B1 | 2/2004 | Blackburn et al. | 435/6 |
| 6,699,667 B2 | 3/2004 | Keen | |
| 6,839,175 B2 | 1/2005 | Washizu | |
| 7,018,795 B2 | 3/2006 | Kinoshita et al. | |
| 7,076,127 B2 | 7/2006 | Washizu | |
| 7,077,982 B2 | 7/2006 | Kinoshita et al. | |
| 7,088,514 B2 | 8/2006 | Kinoshita et al. | |
| 2002/0139961 A1 | 10/2002 | Kinoshita et al. | |
| 2002/0168291 A1 | 11/2002 | Kinoshita et al. | |
| 2002/0168666 A1 | 11/2002 | Kinoshita et al. | |
| 2002/0168667 A1 | 11/2002 | Kinoshita et al. | |
| 2002/0168756 A1 | 11/2002 | Kinoshita et al. | |
| 2003/0003476 A1 | 1/2003 | Kinoshita et al. | |
| 2003/0179381 A1 * | 9/2003 | Kinoshita et al. | 356/450 |
| 2004/0136643 A1 | 7/2004 | Washizu et al. | |
| 2005/0202495 A1 | 9/2005 | Kinoshita et al. | |
| 2006/0029970 A1 | 2/2006 | Kinoshita et al. | |
| 2006/0119921 A1 | 6/2006 | Kinoshita et al. | |
| 2006/0199215 A1 | 9/2006 | Kinoshita et al. | |

FOREIGN PATENT DOCUMENTS

| | | |
|---|---|---|
| GB | 2 245 971 A1 | 1/1992 |
| JP | 63-222248 | 9/1988 |
| JP | 03-282348 | 12/1991 |
| JP | 04-009743 | 1/1992 |
| JP | 04-052546 | 2/1992 |
| JP | 07/075598 | 3/1995 |
| JP | 7-509565 | 10/1995 |
| JP | 9-512345 | 12/1997 |
| JP | 11-183479 | 7/1999 |
| JP | 2000-004054 A | 1/2000 |
| JP | 2000-249644 | 9/2000 |
| WO | WO 94/03774 | 2/1994 |
| WO | WO 96/26435 | 8/1996 |
| WO | WO 01/12665 A2 | 2/2001 |

OTHER PUBLICATIONS

Munekazu Date, et al., "52.3: Direct-viewing Display Using Alignment-controlled PDLC and Holographic PDLC," SID 00 Digest pp. 1184-1187.

Robert J. Collier, et al, "Optical Holography," Chapter 9, §§9.1 & 9.2, pp. 228-233. Academic Press, New York.

Baril et al, "Chromatography of ribonuclease treated myosin extracts from early embryonic chick muscle," Science (1964) 146:413-414.

Liu, et al., "Cell-ELISA using B-galactosidase conjugated antibodies" Journal of Immunological Methods 234 (Feb. 2000) p. 153-167).

Buchel, M. et al., "Langmui-Blodgett-Kuhn Multilayers of Polyglutamates with Azobenzene Moieties: Investigations of Photoinduced Changes in the Optical Properties and Structure of the Films," Langmuir 1995, vol. 11, p. 4460-4466.

Menzel, H. et al., "Small-Angle X-ray Scattering and Ultraviolet-Visible Spectroscopy Studies on the Structure and Structural Changes in Langmuir-Blodgett Films of Polyglutamates with Azobenzene Moieties Tethered by Alkyl Spacers of Different Lengths" Langmuir 1994, vol. 10, p. 1926-1933.

Okahata, Y. et al., "Orientation of DNA Double Strands in a Langmuir-Blodgett Film," Langmuir 1966, vol. 12, p. 1326-1330.

Parazak, D.P. et al., "Comparison of Host-Guest Langmuir-Blodgett Multilayer Formation by Two Different Amphiphilic Cyclodextrins," Langmuir 1996, vol. 12, p. 4046-4049.

Greenham et al, "Charge separation and transport in conjugated-polymer/semiconductor-nanocrystal composites studied by photoluminescence quenching and photoconductivity," Physical Review-B, 1996, 54(24), pp. 17628-17637.

S. Sugai et al., Poly(γ-alkyl Glutamates), Journal of Polymer Science: Part A-2, vol. 4, 183-198 (1966).

Crick, F.H.C., The Packing of α-Helices: Simple Coiled-Coils, Acta Cryst (1953) 6, 689-697.

Minamoto, Y. et al., Polymethylglutamate as a New Matrix for Covalentaly Immobilized Enzymes: Preparation and Properties of Urease and Uricase, Biotech and Bioeng'n, vol. XXII, pp. 1225-1235 (1980).

Kinoshita, T., "Structural color forming system composed of polypeptide-based LB films," *Nanotechnology and Nano-Interface Controlled Electronic Devices*, Chapter 13, 2003, pp. 233-252.

Miyagi, T. "Structural Color with Polypeptide LB Film," *Transactions of the Materials Research Society of Japan*, 27 3, 555-558 (2002).

"Control of Superfine Structure of Membrane and Their Characterization", Polymer, vo. 50, Takatoshi, Kinoshita, Department of Engineering, Nagoya Institute of Technology, pp. 648-651, Sep. 2001.

"A Device for Visual Detection of Antigens and Antibodies by Means of Light Interference", Thin Solid Films, vol. 91, Takeyuki Kawaguchi et al, pp. 369-381, 1990.

Color Tone Control By External Stimuli, Nagoya Institute of Technology, Imitating Function of Bio-skins Applicable to Display Devices, *Nikkan Kogyo Shinbun*, Dec. 28, 2000, Japan.

T. Doi et al., Symposium: Building of Molecular Composition and Its Function, Building and control of peptide type signal transfer function, A506, Nagoya Institute of Technology, Symposium held by JST, Nov. 28, 2000, Japan.

H. Yokoi et al., Preparation of Amphiphilic α-helix LB film, *Polymer Preprints, Japan*. vol. 49 No. 12 IS07, Nagoya Institute of Technology, 2000, Society of Polymer Science, Japan.

H. Yokoi et al., Evaluation of molecular orientation of amphiphilic α-helix water surface monomolecular film, *Polymer Preprints, Japan*, vol. 49 No. 13 lipd090, Nagoya Institute of Technology, 2000, Society of Polymer Science, Japan.

Y. Okahata, Sensing of Odorous and Bitter Substances by using a Bilayer Molecular Film-coated Quartz Oscillator, *Biophysics*, vol. 28. No. 6 Pandect, Tokyo Institute of Technology, 1988, Japan.

Y. Okahata, Prospect for Chemical Information Conversion Membrane, Molecular Recognition to be realized on a Lipid Bilayer Molecular Membrane, *SEN-I GAKKAISHI (Fiber and Industry)* vol. 46, No. 2 Feature: Functional Macromolecular Membranes Films, 1990, Japan.

K. Ariga et al., Evaluation of the Viscoelasticity of the Membrane with the Use of a Quartz Oscillator, Phase Transition of the LB film, vol. 28 No. 11, Tokyo Institute of Technology, 1990, Japan.

H. Yokoi et al., *The 48th Symposium on Macromolecules*, The Two Dimensional Orientation Control of Amphiphilic α-helix Molecule, II P f094, Nagoya Institute of Technology, Oct. 6, 1999, Niigata, Japan.

H. Yokoi et al., *The 49th Annual Meeting of the Society of Polymer Science*, Japan (SPSJ), The pH Dependence of Molecular Orientation in Monolayer Composed of Amphiphilic α-helix Molecule at Air-water Interface, 1 p. 173, Nagoya Institute of Technology, May 29, 2000, Nagoya, Japan.

H. Yokoi et al., *The 49th Symposium on Macromolecules*, Preparation of LB Film consisting of Amphiphilic α-helix Molecule, IS 07, Nagoya Institute of Technology, Sep. 27, 2000, Sendai, Japan.

H. Yokoi et al., *The 49th Symposium on Macromolecules*, "Evaluation of molecular orientation of amphiphilic α-helix water surface monomolecular film", IIPd090, Nagoya Institute of Technology, Sep. 27, 2000, Sendai, Japan.

Y. Nagata, et al., *The 43rd Annual Meeting of the Society of Polymer Science*, Japan (SPSI), "Preparation and Function of Polypeptide Containing a Substrate-binding Site at the Molecular Terminal", Nov. 9, 2006, Nagoya Institute of Technology, and National Institute of Materials and Chemical Research, Tsukuba, May 26, 1994, Nagoya, Japan.

H. Hosokawa et al., *The 44th Annual Meeting of the Society of Polymer Science*, Japan (SPSJ), "Functional Control of Polypeptide Containing an Inclusion Terminal Group", II Pel 119, May 30, 1995, Yokohama, Japan.

H. Hosokawa et al., "Functional Control of Polypeptide Containing an Inclusion Terminal Group", Preprints of Annual meeting of the Society of Fiber Science and Technology, Japan, G-264 3G17, Jun. 29, 1995, Tokyo (Sen-I Gakkai).

H. Hosokawa et al., *45th Annual Meeting of Society of Polymer Science of Japan*, Monolayer of polypeptide containing a cyclodextrin at the terminal, IIIPb100, Nagoya Institute Technology, Nagoya and National Institute of Materials and Chemical Research, Tsukuba, May 29, 1996, Nagoya, Japan.

H. Hosokawa et al., *45th Symposium of Society of Polymer Science of Japan*, Molecular orientation of polypeptide containing a cyclodextrin at the terminal in the monolayer and its function, 2Pb44, Nagoya Institute of Technology, Oct. 2, 1996, Hiroshima, Japan.

H. Hosokawa et al., *46th Annual Meeting of Society of Polymer Science of Japan*, Structural control of polypeptide containing an active site at the terminal in monolayer and its function, IIPb108, Nagoya Institute of Technology, May 24, 1997, Tokyo, Japan.

A. Kato et al., *47th Annual Meeting of Society of Polymer Science of Japan*, Characterization of polypeptide monolayer containing the molecular recognition site, IIIPd124, Nagoya Institute of Technology, May 29, 1998, Kyoto, Japan.

A. Kato et al., *29th Annual Meeting of Union of Chemistry-Related Societies in Chubu Area*, Japan, Characterization of polypeptide monolayer containing a cyclodextrin at the terminal, IB0705, Nagoya Institute of Technology, Oct. 3, 1998, Toyohashi, Japan.

H. Yokoi et al., The control of molecular orientation in monolayer of amphiphilic α-helix, *Preprints presented at 15th Symposium of Membrane Science and Technology*, 3PA53, Nagoya Institute of Technology and Core Research for Evolutional Science and Technology, May 12, 1999, Chiba, Japan (Sen-I Gakkai).

T. Doi et al., *48th Symposium of Society of Polymer Science of Japan*, The molecular orientation and oscillation of polypeptide monolayer at oil/water interface, IIIJ02, Nagoya Institute of Technology and Core Research for Evolutional Science and Technology, Oct. 8, 1999, Niigata, Japan.

T. Doi et al., *Open Symposium of Creation and Functions of New Molecules and Molecular Assemblies sponsored by Core Research for Evolutional Science and Technology (CREST)*, Creation of peptide-type signal transmitting function and control of its function, A506, Nagoya Institute of Technology, Nov. 28, 2000, at Japan Science and Technology Corporation (JST), Tokyo, Japan.

"Molecular alignment of poly(γ-methyl-L-glutamate) containing a β-cyclodextrin at the terminal and molecular identification (n-hexane/water interface)", Control of molecular alignment of polypeptide molecular film published by Dr. Tomokiyo Doi, chapter 4, 2000.

"The Control of Structure and Functions of LB-Film composed of Bio-Related Polymers", First International Symposium on Biometic Materials Processing, Tomokiyo DOI, et al., pp. 19, Jan. 11, 2001.

"Preparation of a Structural Color Forming System by Polypeptide-Based LB Films", The fourth NIMC International Symposium on Photoreaction Control and Photofunctional Materials, Takatoshi Kinoshita, pp. 1-9 and 1-12, Mar. 14, 2001.

"Nano-Phase Separation in the Monolayer Composed of α-Helical Copolypeptide at Air/Water Interface," Chemistry Letters 2000, Hidenori Yokoi, et al., pp. 1210-1211, The Chemical Society of Japan.

"The Molecular Recognition and Polypeptide Orientation in the Monolayer at Oil/Water Interface", 12th Academic Symposium of MRS-Japan manuscripts., Dec. 7, 2000, Kanagawa Y. Mouri, et al., p. 66.

"The Molecular Orientation of a Peptide-based Amphiphile at Hexane/Water Interface", Chemistry Letters 1997, Hirofumi Hosokawa, et al., pp. 745-745, The Chemical Society of Japan.

"The guest-induced oscillation of a monolayer composed of polypeptide containing β-cyclodextrin at the terminal", Chaos, vol. 9, No. 2, 1999, T. Kinoshita, et al., pp. 276-282, American Institute of Physics.

"Structural color forming system composed of polypeptide-based LB films", Nanotechnology and Nano-Interface Controlled Electronic Devices, T. Kinoshita, et al., pp. 233-252, 2003.

"Structural Color with Polypeptide LB Film", Transactions of the Materials Research Society of Japan 27 [3], T. Miyagi, et al., pp. 555-558, 2002.

"Polypeptide membranes at an interface", Prog. Polym. Sci., H. Yokoi, et al., pp. 341-357, 2003.

Sakurai, T., et al, "Characterization of Self-Assembled Monolayer of Polypeptide on Au(111) Surface," Polymer Preprints, Japan 48(13) 3685-3686 (1999).

Chudinova, G.K., et al., "The Study of the Antigen-Antibody reaction by Fluorescence Method in LB films for Immunosensor," *The Solid Films*, 307 (1997) 294-297.

Higuchi et al., "Photocontrol of Molecular Orientation of a Photoresponsive Amphiphilic alpha-Helix in a Lipid Monolayer," *Langmuir*, 1997, 13, 1616-1622.

* cited by examiner (emphasized)
$$\lambda = \frac{2h}{m} \sqrt{n^2 - \sin^2 \alpha} = \frac{2d \cdot \ell}{m} \sqrt{n^2 - \sin^2 \alpha}$$

(enfeebled)
$$\lambda = \frac{4h}{2m-1} \sqrt{n^2 - \sin^2 \alpha} = \frac{4d \cdot \ell}{2m-1} \sqrt{n^2 - \sin^2 \alpha}$$

$(m=1,2,3 \cdots)$

Capture of detection target

TARGET DETECTING APPARATUS, TARGET DETECTION METHOD AND TARGET DETECTION SUBSTRATE

BACKGROUND OF THE INVENTION

1. Field of the Invention

The present invention relates to a target detecting apparatus and target detection method which can detect targets such as pathogens, biological substances and toxic substances efficiently, reliably, simply and with high sensitivity, and to a target detection substrate which can suitably be used in this apparatus and method.

2. Description of the Related Art

In the related art, various kinds of methods have been considered for detecting targets such as pathogens, biological substances and toxic substances, for example, enzyme immunoassay methods such as ELISA. However, in these methods, there was the problem of having to use expensive fluorescent labels or dangerous radiation markers.

Recently, an apparatus and method have been proposed which detect targets by detecting an interference color change of interference light by unit of a detection layer without using a fluorescence label or a radiation marker. For example, an apparatus has been proposed which measures a thickness change of a nonspecific protein layer as an interference color change using an ellipsometer or the like (e.g., JP-A No. 2002-122603 and JP-A No. 2002-116208). In another method, a thickness change is detected as an interference color change in a light reflecting surface by a nucleic acid chain (e.g., JP-B No. 07-32720, JP-A No. 10-288616 and JP-A No. 2001-235473). An apparatus has been proposed wherein light emitted from a light source is irradiated onto a sample surface via a polarizer, the reflected light is reflected by a polarization modulator, and then detected via a polarizer (e.g., JP-A No. 61-34442, JP-A No. 04-78122, JP-B No. 62-57936 and U.S. Pat. No. 4,332,476). Moreover, an apparatus has been proposed which measures a thickness change of a nonspecific protein layer as an interference color change using an ellipsometer or the like, and detects this interference light via a polarizer (e.g., JP-A No. 2002-122603).

However, simple and quick measurement cannot be performed in these cases, and there are problems in that the apparatus easily picks up measurement noise, the measurement error is large, measurement sensitivity is poor and a quantitative measurement cannot be made. Therefore, in the present situation, there was no target detecting apparatus and target detecting method which could detect targets such as pathogens, biological substances and toxic substances without using a costly measuring apparatus, which could detect them with a low measurement error, high efficiency, simplicity, rapidity and sensitivity, and make a quantitative measurement, nor a target detection substrate which could be used in such an apparatus and method, and so the development thereof was eagerly awaited.

Objects and Advantages

It is therefore an object of the present invention to provide a target detecting apparatus and target detecting method which can detect targets such as pathogens, biological substances and toxic substances without using a costly measuring apparatus, which can detect these targets with a low measurement error, high efficiency, simplicity, speed and sensitivity, and make a quantitative detection thereof, and to provide a target detection substrate which can be used in such an apparatus and method.

SUMMARY OF THE INVENTION

The target detecting apparatus of the present invention is a target detecting apparatus comprising an optical irradiation unit to irradiate light, an optical interference unit which can interact with the detection target, which interferes with light irradiated from the optical irradiation unit and radiates it as interference light, and is able to vary the wavelength of the interference light after interaction with the detection target, and a wavelength change detecting unit provided in the path of the interference light, which detects a wavelength change of the interference light radiated by the optical interference unit. In this target detecting apparatus, the optical irradiation unit irradiates light. The optical interference unit interferes with the light irradiated from the optical irradiation unit, and radiates as an interference light. The optical interference unit can interact with the detection target, and after interacting with the detection target, the wavelength of the interference light is changed. The wavelength change detecting unit detects the wavelength change of the interference light radiated by the optical interference unit. As a result, due to the wavelength change of the interference light detected by the wavelength change detecting unit, the interaction of the detection target with the optical interference unit, i.e., the presence of the detection target in the sample, can be detected.

The target detection substrate of the present invention comprises a film-like material on a substrate which can interact with the detection target, interferes with the irradiated light and radiates it as interference light. After it has interacted with the target, it can change the wavelength of the interference light. The target detection substrate, which comprises a film-like material on a substrate and interferes with the irradiated light so as to radiate it as interference light, causes a wavelength change of the interference light before and after the interaction of the detection target and film-like material. This can be applied to a detection system which detects a detection target by detecting this wavelength change. Hence, this target detection substrate can conveniently be used in the target detecting apparatus.

The target detection method of the present invention comprises an optical irradiation step which irradiates light to an optical interference unit which can interact with the detection target, and radiates the light as an interference light, and a wavelength change detection step which detects the wavelength change of the interference light. In this target detection method, light is irradiated to the optical interference unit which can interact with the detection target, and is radiated as an interference light in the optical irradiation step. In the wavelength change detection step, the wavelength change of the interference light is detected. For this reason, due to the wavelength change of the interference light detected by the wavelength change detecting unit, the interaction of the target with the optical interference unit, i.e., the presence of the detection target in the sample, can be detected with simplicity and high precision.

Figure 1:
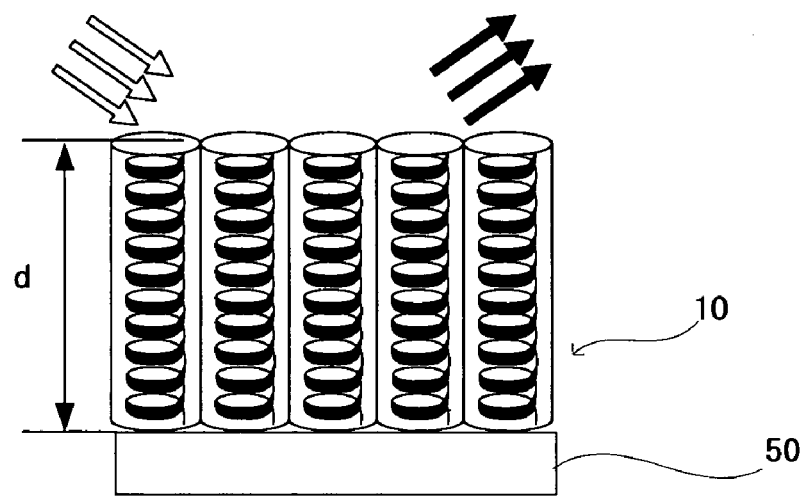
FIG. 1 is a schematic view for explaining structural color formation (occurrence of an interference color) by a monomolecular film (film-like material) of rod-shaped organic molecules (rod-shaped materials) provided on a substrate.

DESCRIPTION OF THE PREFERRED EMBODIMENTS (Target Detecting Apparatus)

The target detecting apparatus of the present invention comprises an optical irradiation unit, an optical interference unit, a wavelength change detecting unit and other unit which may be suitably selected as required.

<Optical Irradiation Unit>

The optical irradiation unit is not particularly limited provided that it irradiates light, and may be selected according to the purpose from light sources known in the art such as for example a halogen lamp (e.g., xenon lamp) or a laser light irradiation device.

Among these, a laser light irradiation device is preferred as it can irradiate a linear luminous flux. In this case, it is easy to control the incidence angle of the light irradiated from this optical irradiation unit to the optical interference unit. Other advantages are that the area of the light-receiving surface in the optical interference unit irradiated by light from the optical irradiation unit can be designed small; that the light-receiving surface of the wavelength change detecting unit which detects the wavelength change of the interference light due to the optical interference unit, can be designed small; that measurement noise can be controlled; and that measurement errors can be reduced.

In the present invention, when a spectrophotometer is used as the wavelength change detecting unit, a light source built into this spectrophotometer can be used as the optical irradiation unit.

<Optical Interference Unit>

The optical interference unit has the functions of interfering with the light irradiated from the optical irradiation unit and being able to interact with the detection target. It interferes with the light irradiated from the optical irradiation unit and radiates it as an interference light, and changes the wavelength of the interference light after interaction with the detection target. The radiation may be reflected light or transmitted light.

As the optical interference unit, the target detection substrate of this the invention is particularly suitable.

The optical interference unit is not particularly limited as long as it has the functions and can be suitably selected according to the purpose, for example comprising at least a film-like material wherein a rod-shaped material is aligned.

Among these, a film-like material wherein a rod-shaped material is aligned on a substrate is preferred. In this case, as the film-like material is provided on the substrate, the structural stability of this film-like material and surface smoothness are excellent, and detection errors can be reduced.

Substrate

The substrate is not particularly limited as long as the film-like material can be arranged on its surface, and can be selected according to the purpose, but for example, from the viewpoint of reducing detection errors, it preferably has excellent surface smoothness, examples are one or more selected from among semiconductors, ceramics, metals, glass and plastics, or an interference filter or pigment filter. The semiconductor may be selected from among those known in the art, e.g., silicon.

Among these substrates, those comprising an identical refractive index film having a substantially equivalent refractive index to that of the rod-shaped material forming the film-like material on the surface, are preferred. In this case, the thickness of the film-like material which is further provided on this substrate can be made thin, the optical interference unit can be easily manufactured at low cost, and the wavelength of the interference light can be easily adjusted to the visible light region. Depending on the thickness and quality of the material of the oxide film, the interference light due to this substrate may show an interference color, and in this case it can also be used as a "pre-colored substrate".

The thickness of the identical refractive index film varies with the refractive index of the rod-shaped material and cannot be uniquely specified, but it is of the order of 50 nm to 1 μm.

This equivalent refractive index film can be formed according to methods known in the art, for example vacuum film-forming methods such as the CVD method and PVD method, or thermal oxidation methods. As an example, when the substrate is a silicon substrate, it can be formed as an oxide film by heating this silicon substrate at 900° C. to 1000° C.

Among the substrates, those comprising a different refractive index film having a different refractive index from that of the film-like material on the surface, are also preferred. In this case, as the substrate comprises a different refractive index film having a different refractive index from the film-like material on the surface, interference light having a sharp spectral curve can be radiated, and even if the wavelength change (wavelength shift) of this interference light is very small, it can be detected simply, reliably, rapidly and with high sensitivity.

The different refractive index film may also have a different refractive index from that of the substrate and may comprise two or more films, and if there are two or more films, their respective different refractive indices may also be mutually different.

The different refractive index film is not particularly limited and may be suitably selected according to the purpose, but a dielectric film may for example be mentioned.

Materials for the dielectric film include, for example, $TiO_2$, $CeO_2$, $Ta_2O_5$, $ZrO_2$, $Sb_2O_3$, $HfO_2$, $La_2O_3$, $MgO$, $Al_2O_3$, $SiO_2$, $In_2O_3$, $ZnO$, $SnO_2$, $Cd_2SnO_4$, $CdIn_2O_4$, $Zn_2SnO_4$, $ZnSnO_3$, $MgIn_2O_4$, $Zn_2In_2O_5$, and $In_3Sn_3O_{12}$, among which $TiO_2$ and $SiO_2$ are preferable.

The interference filter may be selected from among those known in the art, and commercial filters may also be used. In this case, a sharp interference light with a sharp spectral curve can be radiated, and even if the wavelength change (wavelength shift) of this interference light is very small, it can be detected simply, reliably, rapidly and with high sensitivity, which is advantageous. Also, the thickness of the film-like material further provided on this substrate can be made thin, and as a result, the optical interference unit can be manufactured easily and the target detecting apparatus can also be designed as a transmission type apparatus.

The interference filter may be a monochrome filter which extracts a narrow wavelength band (50 nm or less), or it may be a relatively wideband filter such as a dielectric multilayer film, MDM type (e.g., metal/dielectric/metal) or DMD type (e.g., dielectric multilayer film/metal/dielectric multilayer film). In these cases, the dielectric may be formed of an inorganic substance, or may be formed of an organic substance.

In the present invention, the interference filter may also comprise a different refractive index film of different refractive index from the refractive index of the film-like material, on the surface of the substrate.

Film-Like Material

The film-like material is not particularly limited and may be suitably selected according to the purpose, for example it may be formed from the rod-shaped material.

The thickness of the film-like material may be suitably selected according to the wavelength of the interference light before and after wavelength change, the refractive index of the substrate, etc., but for example, it is preferably 50 nm to 1 μm.

In the present invention, one or more films may be provided on the surface of the film-like material. This film is not particularly limited and may be selected according to the purpose, but it is preferred that the film has a refractive index which is substantially equivalent to that of the refractive index of the substrate surface in contact with the film-like material. In this case, even an interference light having a sharp spectral curve can be radiated, and even if the wavelength change (wavelength shift) of this interference light is very small, it can be detected simply, reliably, rapidly and with high sensitivity.

The film is not particularly limited, and may be selected according to the purpose. For example, a dielectric film is preferred.

The dielectric film can be formed on the surface of the film-like material by any method known in the art. Specifically, the material of the dielectric may be selected from gold, silver, platinum, platinum or palladium, these materials being formed as a thin layer by an ion coater or the like, on the surface of the film-like material. The material of the dielectric is not limited to the above, and may also be an oxide such as silicon oxide.

In an aspect wherein the optical interference unit or target detection substrate of the present invention comprises the dielectric film on the surface of the film-like material, the whole optical interference unit or whole target detection substrate functions as the interference filter. In this case, in addition to the target detecting apparatus or the target detection method of the present invention, this target detection substrate may also be used in fields such as colorimetery, flame photometry, monochromators, lasers, optical communications and optical recording.

Rod-Shaped Material

The rod material is not particularly limited and can be suitably selected according to the purpose, for example a rod-shaped inorganic molecule or a rod-shaped organic molecule.

One of these may be used alone, or two or more may be used together. Among these, a rod-shaped organic molecule is preferred from the viewpoints that it easily interacts with the detection target, molecular treatment is easy, formation of the film-like material is easy, and even if the surface quality of the undersurface of the film-like material is not smooth, the surface on the opposite side can easily be maintained smooth.

The rod-shaped organic molecule is not particularly limited and can be suitably selected according to the purpose, e.g., a biopolymer or a polysaccharide. Examples of the biopolymer are a fibrous protein, an α-helix polypeptide and a nucleic acid (DNA, RNA). Examples of this fibrous protein are those having an α-helix structure such as α-keratin, myosin, epidermin, fibrinogen, tropomycin and silk fibroin.

The polysaccharide may for example be amylose or the like.

From the viewpoint of maintaining the stability rod-shape of the organic molecule, a helical molecule wherein the molecule has a helical structure is preferred. In this case, even if the surface quality (e.g., the surface quality of the substrate) of the undersurface of the film-like material is not smooth, the surface (upper surface) (surface on which light is incident from the optical irradiation unit) on the opposite side can easily be maintained smooth, and measurement errors of wavelength variation produced when the surface is not smooth, can be reduced.

Among those mentioned above, the spiral molecule may be an α-helix polypeptide, DNA, amylose, etc.

α-Helix Polypeptide

The α-helix polypeptide is one of the secondary structures of a polypeptide. It is rotated once (forms one spiral) every 3.6 aminoacid residues, forms substantially parallel hydrogen bonds with the spiral axis between the imido group (—NH—) and carbonyl group (—CO—) every fourth aminoacid, and has a structure which is stable energywise due to the repetition of 7 aminoacids as one unit.

The direction of the helix of the α-helix polypeptide is not particularly limited, and may be right-handed or left-handed. Due to stability factors, only α-helix polypeptides having a right-handed helix are found in nature.

The aminoacid which forms the α-helix polypeptide is not particularly limited and may be selected according to the purpose if it can form an α-helix structure. Aminoacids which can easily form this α-helix structure are preferred, examples of such aminoacids being aspartic acid (Asp), glutamic acid (Glu), arginine (Arg), lysine (Lys), histidine (His), asparagine (Asn), glutamine (Gln), serine (Ser), threonine (Thr), alanine (Ala), valine (Val), leucine (Leu), isoleucine (Ile), cysteine (Cys), methionine (Met), thyrosin (Tyr), phenylalanine (Phe) and tryptophan (Trp). One of these may be used alone, or two or more may be used together.

By suitably selecting the aminoacid, the α-helix polypeptide can be designed to have hydrophilicity, hydrophobicity or amphiphilicity. If hydrophilicity is conferred, the aminoacid may for example be serine (Ser), threonine (Thr), aspartic acid (Asp), glutamic acid (Glu), arginine (Arg), lysine (Lys), asparagine (Asn) or glutamine (Gln). If hydrophibicity is to be conferred, the aminoacid may for example be phenylalanine (Phe), tryptophan (Trp), isoleucine (Ile), thyrosin (Tyr), methionine (Met), leucine (Leu) or valine (Val).

The aminoacid forming the α-helix polypeptide is not particularly limited, and may for example be a L-amino acid or D-amino acid, or a derivative thereof wherein the side chains are modified.

In the α-helix polypeptide, by esterifying the carboxyl group in the amino acid which forms this α-helix which does not form a peptide linkage, hydrophobicity can be conferred by esterification, or hydrophilicity can be conferred by hydrolyzing this esterified carboxyl group.

The number of linkages (polymerization degree) of the aminoacid in the α-helix polypeptide is not particularly limited and can be suitably selected according to the purpose, but it is preferably 10 to 5000.

If the number of linkages (polymerization degree) is less than 10, the polyaminoacid may not be able to form a stable α-helix, and if the number of linkages (polymerization degree) is more than 5000, it may become difficult to orient it in a perpendicular direction.

Examples of the α-helix polypeptide are polyglutamic acid derivatives such as poly(γ-methyl-L-glutamate), poly(γ-ethyl-L-glutamate), poly(γ-benzyl-L-glutamate), poly(L-glutamine acid-γ-benzyl) and poly (n-hexyl-L-glutamate), polyaspartic acid derivatives such as poly(beta-benzyl-L-aspartate), poly(L-leucine), poly(L-alanine), poly(L-methionine), poly(L-phenylalanine), and poly(L-lysine)-poly(γ-methyl-L-glutamate).

The α-helix polypeptide may be suitably be synthesized or prepared by a method known in the art, or the commercial product may be used.

As an example of the synthesis of the α-helix polypeptide, the block copolypeptide [poly(L-lysine)$_{25}$-poly(γ-methyl-L-glutamate)$_{60}$] PLLZ$_{25}$-PMLG$_{60}$ may be synthesized as follows. The block copolypeptide [poly(L-lysine)$_{25}$-poly(γ-methyl-L-glutamate)60] PLLZ$_{25}$-PMLG$_{60}$, is synthesized by polymerizing Nε-carbobenzoxy L-lysine N$^{\alpha}$-carboxylic acid anhydride (LLZ-NCA) using n-hexylamine as initiator, and then polymerizing γ-methyl L-glutamate N-carboxylic acid anhydride (MLG-NCA) as shown by the following equation:

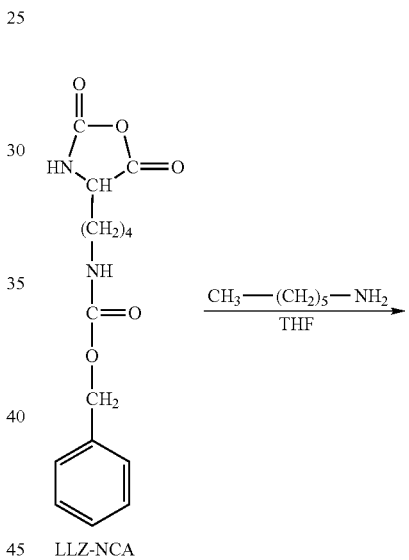

LLZ-NCA

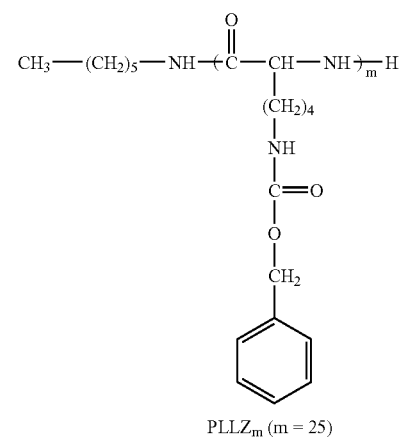

PLLZ$_m$ (m = 25)

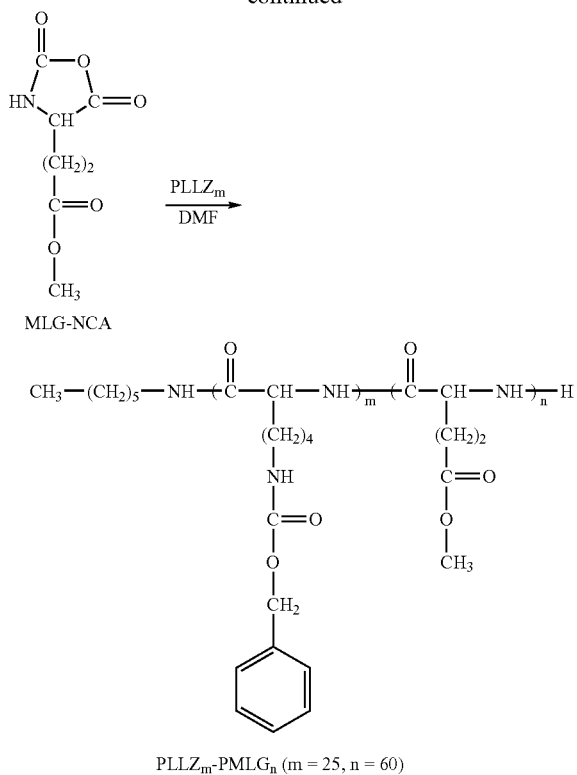

The synthesis of the α-helix polypeptide is not limited to the above, and can also be achieved by genetic engineering. For example, a host cell is transformed by an expression vector incorporating DNA which codes for the polypeptide, and this transformant is then cultured.

Examples of this expression vector are a plasmid vector, a phage vector, or the chimera vector of a plasmid and phage.

Examples of the host cell are prokaryon microorganisms such as *Escherichia coli* and *Bacillus subtilis*, eukaryon microorganisms such as yeast fungus, and animal cells.

The α-helix polypeptide may also be prepared by cutting out the α-helix structure portion from natural fibrous proteins such as α-keratin, myosin, epidermin, fibrinogen, tropomycin and silk fibroin.

DNA

The DNA may be single-stranded DNA, but from the viewpoint of stabilizing the rod shape, it is preferred that it is double-stranded DNA.

The double-stranded DNA has a double helix structure wherein two right-handed helical polynucleotide chains are positioned so that they extend in mutually opposite directions around one central axis.

The polynucleotide chain is formed by four kinds of nucleic acid bases, i.e., adenine (A), thymine (T), guanine (G) and cytosine (C). In the polynucleotide chain, the nucleic acid bases mutually project inside a plane perpendicular to the central axis, forming the so-called Watson-Crick base pairs wherein thymine is specifically hydrogen-bonded to adenine, and cytosine is specifically hydrogen-bonded to guanine, respectively. As a result, in the double-stranded DNA, two polypeptide chains are joined together complementarily.

The DNA can be prepared by the PCR (Polymerase Chain Reaction) method, the LCR (Ligase Chain Reaction) method, the 3SR (Self-sustained Sequence Replication) method and the SDA (Strand Displacement Amplification) method known in the art, but among these, the PCR method is preferred.

The DNA may be directly cut out enzymatically with a restriction enzyme, prepared by a gene cloning method, or prepared by a chemosynthesis method.

In the case of the gene cloning method, the DNA can be prepared in large amounts by incorporating the product of amplifying a normal nucleic acid into a vector selected from a plasmid vector, a phage vector or the chimera vector of a plasmid and phage, and introducing it into an arbitrary host capable of multiplication selected from a prokaryon microorganism such as *Escherichia coli* or *Bacillus subtilis*, eukaryon microorganism such as yeast fungus, or animal cells.

The chemosynthesis method may be a liquid phase process such as the triester method and phosphorous acid method, or a solid phase synthetic process using an insoluble carrier. In the case of the chemosynthesis method, after preparing single-stranded DNA in large amount using an automatic synthesis machine known in the art, double-stranded DNA can be prepared by performing annealing.

Amylose

The amylose is a polysaccharide having a helical structure wherein D-glucose which forms starch, a homopolysaccharide for storing higher plants, is connected in a straight chain by α-1,4 bonds.

The molecular weight of the amylose is preferably of the order of from several thousands to about 150,000 in terms of number average molecular weight.

The amylose may be a commercial product, or may be suitably prepared according to a known method.

Part of the amylose may also contain amylopectin.

The length of the rod-shaped organic molecule is not particularly limited, and can be suitably selected according to the purpose.

The diameter of the rod-shaped organic molecule is not particularly limited, but in the case of the α-helix polypeptide, it is of the order of 0.8 nm to 2.0 nm.

The rod-shaped organic molecule may be completely lipophilic (hydrophobic), hydrophilic, or amphiphilic wherein part is lipophilic (hydrophobic) or hydrophilic, and the other part has the opposite affinity to this part.

The wavelength of the interference light due to the optical interference unit may or may not be in the visible light region. The former case is preferred as the wavelength of the interference light can be detected visually, and it is more preferred that the wavelength of the interference light is in the visible light region after wavelength change. In this case, this interference light can be observed as an interference color, the principle whereby this interference color is observed being based on so-called structural color formation.

Structural Color Formation

Reflection of the incident light as the colored interference light is a color formation (color of interference light) in which, when an external stimulus, such as an electric field, a magnetic field, heat, light (e.g., natural light, infrared light, ultraviolet light), or the like, is applied to the film, light of a specific wavelength is reflected in accordance with the thickness of the film and the refractive index thereof, on the basis of the multilayer thin-film interference theory which is the basic principle of color formation of the scaly powder of the wings of a Morpho butterfly. As a result, color formation (colored interference light) occurs at the surface of the film. In the structural color formation, a dye or pigment is unnecessary.

Hereinafter, the principles of light reflection of incident light as colored interference light will be explained.

Figure 2:
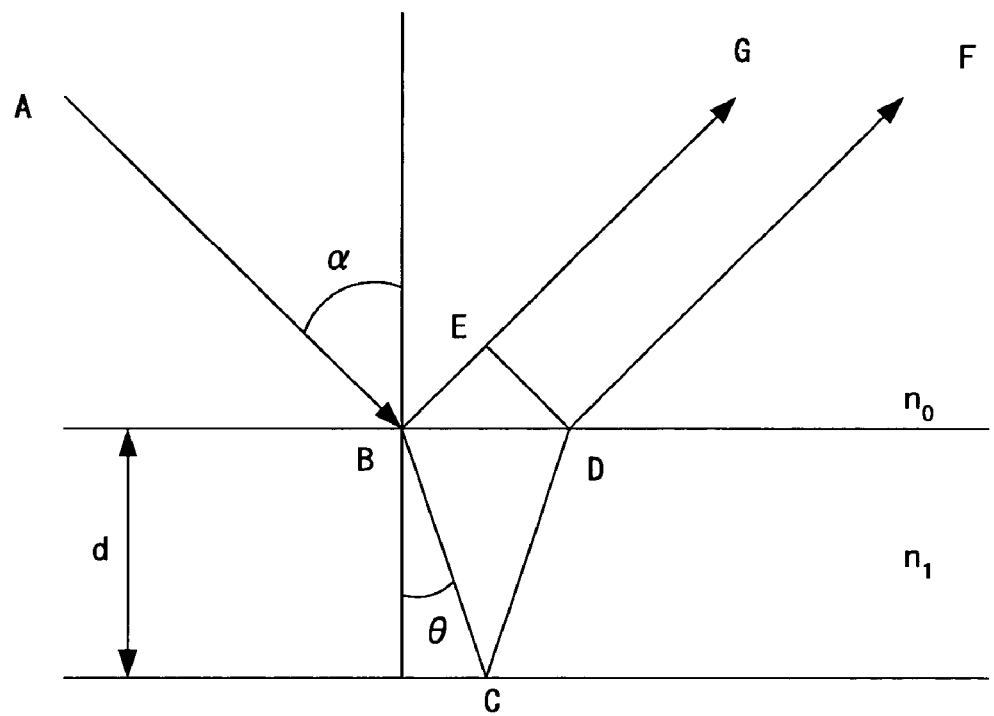
FIG. 2 is a schematic view for explaining the principles of structural color formation.

As shown in FIGS. 1 and 2, the wavelength (λ) of the interference light due to this film-like material (or film-like material formed of the rod-shaped organic material 10 and oxide layer in the substrate 50) when the film-like material (or film-like material formed of the rod-shaped material 10 and oxide layer in the substrate 50), is irradiated by the optical irradiation unit, is emphasized under the conditions shown in the following (1), and enfeebled under the conditions shown in the following (2).

$$\lambda = \frac{2tl}{m}\sqrt{n^2 - \sin^2\alpha} \quad (1)$$

$$\lambda = \frac{4tl}{2m-1}\sqrt{n^2 - \sin^2\alpha} \quad (2)$$

In formula (1) and formula (2), λ is the wavelength (nm) of interference light, α is the incidence angle (°) of light on the film-like material (or film-like material formed of the rod-shaped organic molecules 10 and oxide layer in the substrate 50), "t" is the thickness (nm) of the film-like material (or the film-like material and the oxide layer in the substrate), "l" is the number of the film-like materials (or film-like material and oxide layer in the substrate), "n" is the refractive index of the film-like material (or film-like material formed of the rod-shaped organic molecules 10 and oxide layer in the substrate 50), and "m" is an integer equal to 1 or more.

The thickness of the film-like material (or film-like material formed of the rod-shaped organic molecules 10 and oxide layer in the substrate 50), is preferably 810 nm or less, but more preferably 10 nm to 810 nm.

By suitably changing the thickness, the color (wavelength) of the structural color can be changed.

The film-like material may be a monomolecular film-like material of the rod material, or may be a laminated film-like material of this monomolecular film-like material.

The monomolecular film-like material or the laminated film-like material may be formed for example by a coating method known in the art, or Langmuir-Blodgett's technique (LB method), and in the latter case, the LB film-like material-forming apparatus known in the art (e.g., NL-LB400 NK-MWC, Japan Laser & Electronics Laboratories) can be used.

Figure 3:
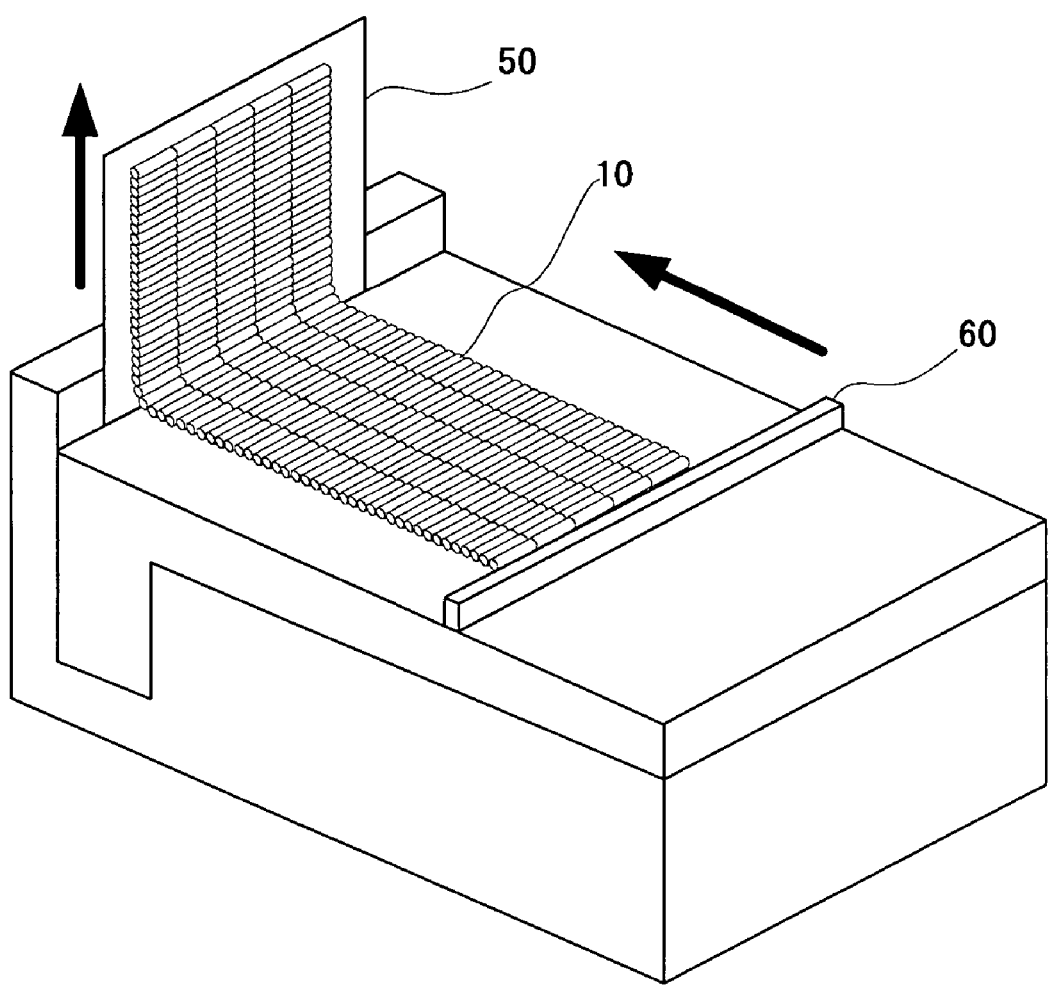
FIG. 3 is a schematic descriptive diagram showing one example of the formation of a monomolecular film (film-like material) by rod-shaped organic molecules (LB method).

The monomolecular film-like material can be formed on the substrate 50 using an extrusion member 60, for example in the state where lipophilic (hydrophobic) or amphiphilic rod-shaped organic molecules are floating on a water surface (aqueous phase), or the state where hydrophilic or amphiphilic rod-shaped organic molecules are floating on an oil surface (oil phase), i.e., a state wherein the rod-shaped organic molecules 10 are oriented as shown in FIG. 3. By repeating this operation, a laminated film comprising a desired number of monomolecular films can be formed on the substrate 50.

At this time, it is preferred to give the surface of the substrate 50 a surface treatment for the purpose of making the rod-shaped organic molecules 10 adhere or bond, for example if the rod-shaped organic molecule 10 (e.g., an α-helix polypeptide) is hydrophilic, it is preferred to first perform a surface treatment beforehand, such as hydrophilization treatment using octadecyl trimethylsiloxane or the like.

Figure 4:
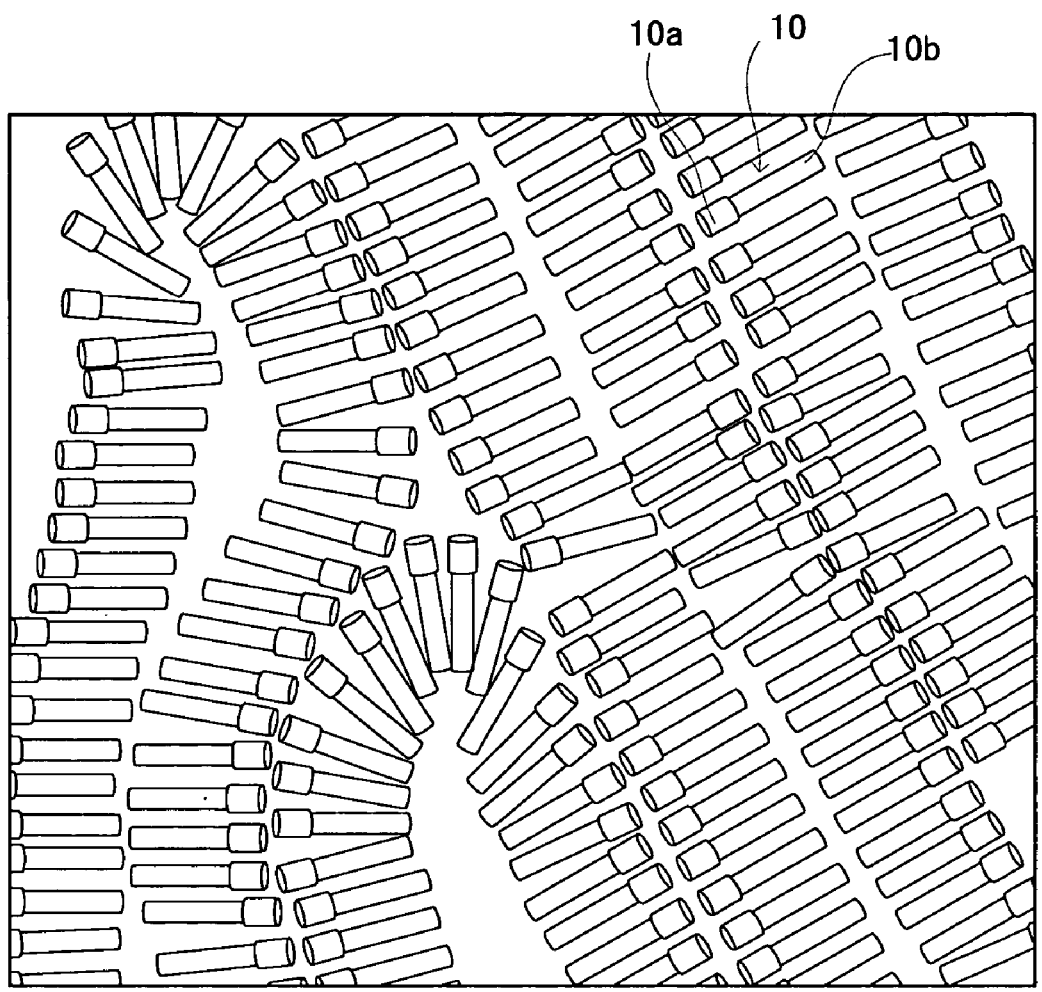
FIG. 4 is a schematic descriptive diagram showing an example of how amphiphilic rod-shaped organic molecules are oriented on water (or an aqueous phase).

When the monomolecular film of amphiphilic rod-shaped organic molecules 10 is formed, the state wherein the rod-shaped organic molecules 10 float on the oil phase or aqueous phase is such that the lipophilic parts (hydrophobic parts) 10a are oriented adjacent to each other, and the hydrophilic parts 10b are oriented adjacent to each other in the rod-shaped organic molecules 10 on the aqueous phase or oil phase, as shown in FIG. 4.

Figure 5A:
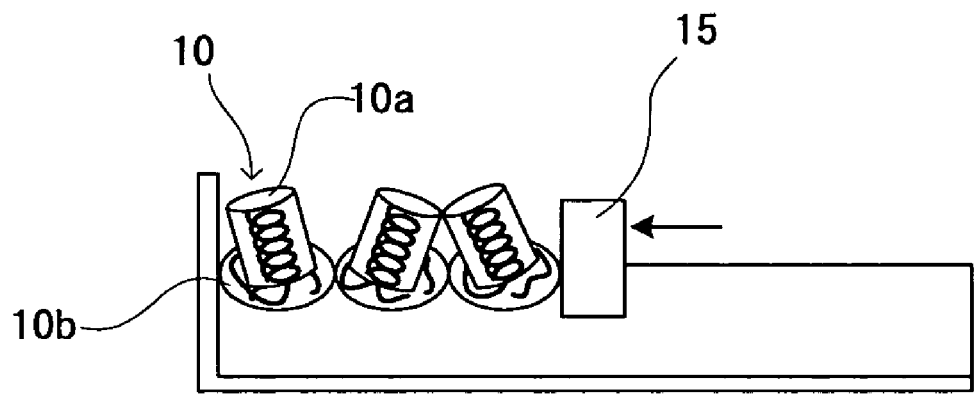
FIGS. 5A and 5B are schematic descriptive diagrams showing an example of a method for standing amphiphilic rod-shaped organic molecules on water (or an aqueous phase).
Figure 5B:
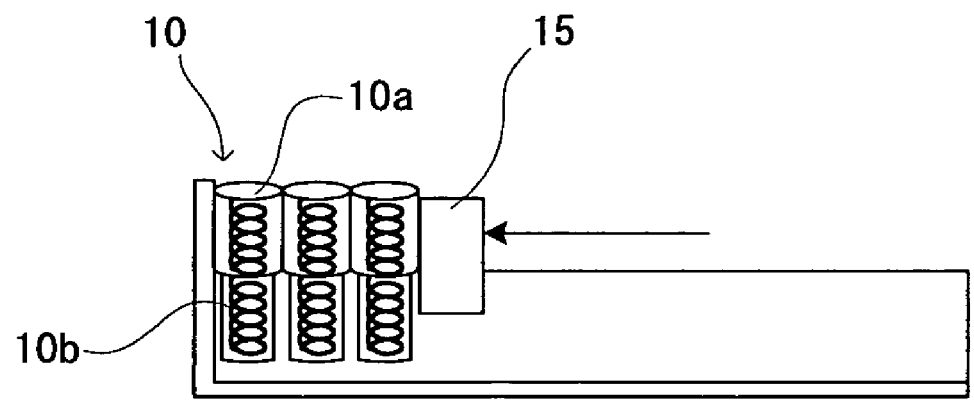

Described above is an example of a monomolecular film wherein the rod-shaped organic molecules are oriented in the plane direction of the monomolecular film (laid horizontally) or a laminated film comprising monomolecular films. A monomolecular film wherein the rod-shaped organic molecules are oriented in the thickness direction of the monomolecular film (standing state) can for example be formed as described below. Specifically, as shown in FIGS. 5A and B, first, the pH of the water (aqueous phase) is adjusted to an alkalinity of about 12 with the amphiphilic rod-shaped organic molecules 10 (α-helix polypeptide) floating on the water surface (aqueous phase). As a result, the hydrophilic parts 10b of the rod-shaped organic molecules 10 (α-helix polypeptide) lose the α-helix structure and take up a random configuration. At this time, the lipophilic parts (hydrophobic parts) 10a of the rod-shaped organic molecules 10 (α-helix polypeptide) retain their α-helix structure. Next, the pH of the water (aqueous phase) is adjusted to an acidity of about 5. As a result, the hydrophilic parts 10b of the rod-shaped organic molecules 10 (α-helix polypeptide) again take up an α-helix structure. At this time, when a pressure member 15 brought into contact with the rod-shaped organic molecules 10 (α-helix polypeptide), the pressure member 15 presses the rod-shaped organic molecules 10 (α-helix polypeptide) by air pressure from the side in the direction indicated by the arrows in FIGS. 5A and 5B, and the rod-shaped organic molecules 10 remain standing on the water (aqueous phase) and the hydrophilic parts 10b become oriented effectively perpendicular to the water surface in the aqueous phase to take up an α-helix structure. Hence, as described above referring to FIG. 3, a monomolecular film can be formed on a substrate 50 by extruding on the substrate 50 using a pressure member 60 with the rod-shaped organic molecules 10 (α-helix polypeptide) aligned in an orderly manner. By repeating this operation, a laminated film comprising the desired number of monomolecular films can be formed on the substrate 50.

Target Interaction Part

In the present invention, it is preferred that the rod-shaped material comprises a target interaction part which is capable of interaction with the detection target. In this case, due to the interaction of this target interaction part of the rod-shaped material with the detection target, a wavelength change appears in the interference light due to the interference unit, and when the wavelength change detecting unit detects this wavelength change, the detection target in the sample can be detected.

The target interaction part is not particularly limited provided that it can interact with the detection target, and may be suitably selected according to the purpose, but it is preferred that it can interact with the detection target by one or both of physical adsorption and chemical adsorption.

The detection target interaction part is not particularly limited and may be suitably selected according to the purpose, but it is preferably a target capturing body which can capture the detection target. In this case, the target capturing body is not directly bonded to the substrate, but the detection capturing body is bonded to the rod-shaped material, and the rod-shaped material is bonded to the substrate, so for example if the target capturing body is an organic substance, instead of bonding this directly to the substrate which is an inorganic substance, it is easier to arrange it on the substrate via a bond with the rod-shaped material which is also an organic substance, and the target capturing body is also thereby stabilized. Further, even if the substrate surface is not smooth, the target capturing body can be laid flat, so the light-receiving surface irradiated by the optical irradiation unit can be smoothed, and measurement errors in the wavelength change of the interference light due to the fact that the light-receiving surface is not smooth, can be reduced.

The target capturing body is not particularly limited provided that it can capture the target, and may be suitably selected according to the purpose.

The form of the capture is not particularly limited, but may be physical adsorption or chemical adsorption. These may for example be realized by hydrogen bonds, intermolecular forces (van der Waals force), coordination bonds, ionic bonds or covalent bonds.

Specific examples of the target capturing body are enzymes, coenzymes, enzyme substrates, enzyme inhibitors, clathrate compounds (hereafter, may be referred to as "host compounds" or "hosts"), metals, antibodies, antigens, proteins, microorganisms, viruses, cell debris, metabolic products, nucleic acids, hormones, hormone receptors, lectins, sugars, physiologically active materials and physiologically active material receptors.

When the target capturing body is an enzyme, the detection target is for example a coenzyme of this enzyme; when it is a coenzyme, the detection target is for example an enzyme for which this coenzyme functions as a coenzyme; when it is a clathrate compound, the detection target is for example a guest compound (included component) of this clathrate compound; when it is an antibody, the detection target is for example a protein which is an antigen to this antibody; when it is a protein, the detection target is for example an antibody to which this protein is an antigen; when it is a nucleic acid, the detection target is for example a complementary nucleic acid to this nucleic acid; when it is a hormone receptor such as tubulin or chitin, it is for example a hormone received by this hormone receptor; when it is a lectin, it is for example a sugar received by this lectin; and when it is a physiologically active material-receiving compound, it is for example a physiologically active material received by this physiologically active material-receptor.

The sample containing the detection target is not particularly limited and may be suitably selected according to the purpose, but examples are pathogens such as bacteria and viruses, blood, saliva, tissue pathology sections and excreta such as feces and urine. When performing a prenatal diagnosis, the sample may be embryo cells in the amniotic fluid or some dividing egg cells in a test-tube. In these samples, cell destructive treatment may be performed, directly or after concentrating as sediment by centrifuging if necessary, using a combination of for example enzyme treatment, heat treatment, surfactant treatment or ultrasonic treatment.

The clathrate compound is not particularly limited providing that it has molecular recognition ability (host-guest bonding ability), and may be suitably selected according to the purpose, examples being those with a cylindrical (one-dimensional) hollow, those with a stratified (two-dimensional) hollow, or those with a cage-shaped (three-dimensional) hollow.

Examples of clathrate compounds comprising a cylindrical (one-dimensional) hollow are urea, thiourea, deoxycholic acid, dinitrodiphenyl, dioxytriphenylmethane, triphenylmethane, methyl naphthalene, spirochroman, PHTP (perhydrotriphenylene), cellulose, amylose and cyclodextrin (in solution, the hollows are cage-shaped).

Examples of detection targets which can be captured by urea are n-paraffin derivatives.

Examples of detection targets which can be captured by thiourea are branched and cyclic hydrocarbons.

Examples of detection targets which can be captured by deoxycholic acid are paraffins, fatty acids and aromatic compounds.

Examples of detection targets which can be captured by dinitrodiphenyl are diphenyl derivatives.

Examples of detection targets which can be captured by dioxytriphenylmethane are paraffin, n-alkene and squalene.

Examples of detection targets which can be captured by triphenylmethane are paraffins.

Examples of detection targets which can be captured by methylnaphthalene are n-paraffins and branched paraffins up to $C_{16}$.

Examples of detection targets which can be captured by spirochroman are paraffins.

Examples of detection targets which can be captured by PHTP (perhydrotriphenylene) are chloroform, benzene and various polymer substances.

Examples of detection targets which can be captured by cellulose are $H_2O_2$, paraffins, $CCl_4$, dyes and iodine.

Examples of detection targets which can be captured by amylose are fatty acids and iodine.

Cyclodextrin is a cyclic dextrin generated by decomposition of the amylase in starch, three types, $\alpha$-cyclodextrin, $\beta$-cyclodextrin and $\gamma$-cyclodextrin being known. In the present invention, cyclodextrin also includes cyclodextrin derivatives wherein some of these hydroxyl groups are replaced by other functional groups, for example, alkyl groups, allyl groups, alkoxy groups, amide groups and sulfonic acid groups.

Examples of detection targets which can be captured by cyclodextrin are phenol derivatives such as thymol, eugenol, resorcinol, ethylene glycol monophenyl ether and 2-hydroxy4-methoxy-benzophenone, benzoic acid derivatives such as salicylic acid, methyl parahydroxybenzoate and ethyl p-hydroxybenzoate, and esters thereof, steroids such as cholesterol, vitamins such as ascorbic acid, retinol and tocopherol, hydrocarbons such as limonene, allyl isothiocyanate, sorbic acid, iodine molecules, methyl orange, Congo Red and 2-p-toluidinylnaphthalene-6-sulfonic acid potassium salt (TNS).

The stratified (two-dimensional) clathrate compound may for example be a clay mineral, graphite, smectite, montmorillonite or zeolite.

Examples of detection targets which can be captured by clay minerals are hydrophilic substances and polar compounds.

Examples of detection targets which can be captured by graphite are O, $HSO_4^-$, halogens, halides and alkali metals.

Examples of detection targets which can be captured by montmorillonite are brucine, codeine, o-phenylenediamine, benzidine, piperidine, adenine, guianine and ribosides thereof.

Examples of a detection target which can be captured by zeolite are $H_2O$ or the like.

The cage-shaped (three-dimensional) clathrate compound may for example be a hydroquinone, gaseous hydrate, tri-o-thymotide, oxyflavane, dicyanoamine nickel, cryptand, calixarene or a crown compound.

Examples of detection targets which can be captured by hydroquinone are HCl, $SO_2$, acetylene and rare gas elements.

Examples of detection targets which can be captured by gaseous hydrates are halogens, rare gas elements and lower hydrocarbons.

Examples of detection targets which can be captured by tri-o-thymotide are cyclohexane, benzene and chloroform.

Examples of detection targets which can be captured by oxyflavane are organic bases.

Examples of detection targets which can be captured by dicyanoamine nickel are benzene and phenol.

Examples of detection targets which can be captured by cryptand are $NH_4^+$ and various metal ions.

Calixarene is a cyclic oligomer wherein phenol units are linked by methylene groups, which can be synthesized under suitable conditions from phenol and formaldehyde, and whereof 4 to 8 nuclides are known. Among these, examples of detection targets which can be captured by p-t-butylcalixarene (n=4) are chloroform, benzene and toluene. Examples of detection targets which can be captured by p-t-butyl calixarene (n=5) are isopropyl alcohol and acetone. Examples of detection targets which can be captured by p-t-butyl calixarene (n=6) are chloroform and methanol. An example of a detection target which can be captured by p-t-butyl calixarene (n=7) is chloroform.

Crown compounds include not only crown ethers having oxygen as an electron-donative donor atom, but also, as an analog, large ring compounds having donor atoms such as nitrogen and sulfur as component atoms of the ring system, and also include complex cyclic crown compounds having two or more rings such as cryptand, for example, cyclohexyl-12-crown-4, dibenzo-14-crown-4, t-butylbenzo-15-crown-5, dibenzo-18-crown-6, dicyclohexyl-18-crown-6, 18-crown-6, tribenzo-18-crown-6, tetrabenzo-24-crown-8 and dibenzo-26-crown-6.

Examples of detection targets which can be captured by the crown compound are various metal ions such as alkaline earth metals, e.g., alkali metals such as Li, Na, K, Mg and Ca, $NH_4^+$, alkylammonium ions, guanidium ions and aromatic diazonium ions, this crown compound forming a complex therewith. Examples of other detection targets which can be captured by this crown compound are polar organic compounds containing C—H (acetonitrile, malonitrile and adiponitrile) having a relatively large acidity, N—H (aniline, aminobenzoic acid, amides and sulfamide derivatives) or O—H units (phenol, acetic acid derivatives), this crown compound forming a complex therewith.

The size (diameter) of the hollow of the clathrate compound is not particularly limited and can be suitably selected according to the purpose, but from the viewpoint of manifesting a stable molecular recognition ability (host-guest bonding ability), it is preferably 0.1 nm to 2.0 nm.

Clathrate compounds may also be classified as, for example, monomolecular host compounds, polymolecular host compounds, polymer host compounds and inorganic host compounds.

Examples of monomolecular host compounds are cyclodextrin, crown compounds, cyclophane, azacyclophane, calixarene, cyclotriveratrylene, spherand, cavitand and oligopeptides.

Examples of polymolecular host compounds are urea, thiourea, deoxycholic acid, perhydrotriphenylene and tri-o-thymotide.

Examples of polymer host compounds are cellulose, starch, chitin, chitosan and polyvinyl alcohol.

Examples of inorganic host compounds are intercalation compounds, zeolite and Hofmann type complexes.

The antibody is not particularly limited provided that it undergoes an antigen-antibody reaction with a specific antigen, but it may be a polyclonal antibody or monoclonal antibody, and further contain IgG, IgM, IgE, Fab', Fab, $F(ab')_2$ of IgG, or avidin.

The antigen is not particularly limited and can be suitably selected according to the type of antibody, for example plasma proteins, tumor markers, apoproteins, virus antigens, autoantibodies, coagulation/fibrinolysis factor, hormones, drugs in blood, HLA antigens and biotin.

Examples of plasma proteins are immunoglobulin (IgG, IgA, IgM, IgD, IgE), complementary components (C3, C4, C5, C1q), CRP, $\alpha_1$-antitrypsin, $\alpha_1$-microglobulin, $\beta_2$-microglobulin, haptoglobin, transferrin, ceruloplasmin and ferritin.

Examples of tumor markers are $\alpha$-fetoprotein (AFP), carcinoembryonic antigen (CEA), CA 19-9, CA125 and CA 15-3, SCC antigen, prostate gland acid phosphatase (PAP), PIVKA-II, $\gamma$-seminoprotein, TPA, Elastase I, nerve specific enolase (NSE) and immunosuppression acidic protein (IAP).

Examples of apoproteins are apo A-I, apo A-II, apo B, apo C-II, apo C-III and apo E.

Examples of virus antigens are hepatitis B virus (HBV)-related antigen, hepatitis C virus (HVC)-related antigen, HTLV-I, HIV, rabies virus, influenza virus and rubella virus.

Examples of HCV-related antigens are HCVc100-3 recombinant antigen, pHCV-31 recombinant antigen and pHCV-34 recombinant antigen, and mixtures thereof may be used. Examples of HIV-related antigens are virus surface antigen, e.g., HIV-I env.gp41 recombinant antigen, HIV-I env.gp120 recombinant antigen, HIV-I gag.p24 recombinant antigen and HIV-II env.p36 recombinant antigen.

Other infections apart from viruses are MRSA, ASO, toxoplasma, mycoplasma and STD.

Examples of autoantibodies are anti-microzome antibody, anti-siloglobulin antibody, antinuclear antibody, rheumatism factor, anti-mitochondrion antibody and myelin antibody.

Examples of coagulation/fibrinolysis factor are fibrinogen, fibrin cleavage product (FDP), plasminogen, $\alpha_2$-plasmin inhibitor, Antithrombin III, $\beta$-thromboglobulin, Factor VIII, Protein C and Protein S.

Examples of hormones are pituitary hormones (LH, FSH, GH, ACTH, TSH, prolactin), thyroid hormones ($T_3$, $T_4$, siloglobulin), calcitonin, parathyroid hormone (PTH), adenocoriticotropic hormones (aldosterone, cortisol), gonad hormone (hCG, estrogen, testosterone, hPL), and pancreatic and gastrointestinal hormones (insulin, C-peptide, glucagon, gastrin). Other examples are (renin, Angiotensin I and II, enkephalin and erythropoietin).

Examples of drugs in blood are antiepileptics such as carbamazepine, primidone and valproic acid, circulatory organ disease drugs such as digoxin, quinidine, digitoxin and theophylline, and antibiotics such as gentamycin, kanamycin and streptomycin.

These proteins may be low molecular weight molecules (about 6000 to 13000) which show high affinity with heavy metals, in particular zinc, cadmium, copper and mercury. The proteins are present in the liver, kidney and other organs of the animal, and have recently been shown to be present also in microorganisms. They have a high cysteine content, and show an aminoacid distribution containing almost no aromatic residues. They are important substances which have detoxication functions, such as eliminating cadmium and mercury from the body, and also participate in the storage and distribution of trace metals indispensable to the living body such as zinc and copper.

Examples of heavy metals are alkyl mercury compounds (R—Hg), mercury or its compounds (Hg), cadmium or its compounds (Cd), lead or its compounds (Pb), hexavalent chromium ($Cr_{6^+}$), copper or its compounds (Cu), zinc or its compounds (Zn), cyan, arsenic, selenium, manganese, nickel, iron, zinc, selenium, and tin.

The method of bonding the target capturing body to the rod-shaped organic molecules (rod-shaped object) is not particularly limited and can be suitably selected according to the type of target capturing object and rod-shaped organic molecules. Examples are methods known in the art, i.e., the method of using covalent bonds such as ester bonds or amide bonds, the method wherein a protein is labeled with avidin, and bonded to a biotin-modified capturing structure, and the method wherein a protein is labeled with streptavidin, and bonded to a biotin-modified capturing structure.

In the target detection apparatus according to the present invention, due to the use of these methods, any desired target capturing body can easily be bonded to the rod-shaped organic molecules, so unlike the case where this target detection body is directly bonded to the substrate, the target capturing body or detection target can be freely selected over a wide range, the detection apparatus can be used for a wide range of applications regardless of the detection purpose or type of detection target, and as the surface of the target capturing body can be kept smooth, wavelength variation unevenness of the interference light and measurement errors are small, so detection can be performed with high sensitivity.

Examples of using covalent bonds are the peptide method, diazo method, alkylation, cyanogen bromide activation, bonding by crosslinking agent, the fixing method using the Ugi reaction, the fixing method using a thiol disulfide exchange reaction, the Schiff base-forming method, the chelate bond method, the tosyl chloride method and biochemical-specific bonding, but to obtain more stable bonds such as covalent bonds, methods using the reaction of a thiol group with a maleimide group, the reaction of a pyridyl disulfide group with a thio group and the reaction of an amino group with an aldehyde group are preferred, and the method of using a chemical binder or crosslinking agent is more preferred.

Examples of such chemical binders and crosslinking agents are carbodiimides, isocyanates, diazo compounds, benzoquinones, aldehydes, periodic acids, maleimido compounds and pyrydyl disulfide compounds. Specific examples thereof are glutaraldehyde, hexamethylene diisocyanate, hexamethylene diisothiocyanate, N,N'-polymethylene bis-iodine acetamide, N,N'-ethylene bis-maleimide, ethylene glycol bis-succinimidyl succinate, bis-diazobenzidine, 1-ethyl-3-(3-dimethyl amino propyl) carbodiimide, succinimidyl 3-(2-pyridyldithio)propionate (SPDP), N-succinimidyl 4-(N-maleimido methyl)cyclohexane-1-carboxylate (SMCC), N-sulfosuccinimidyl 4-(N-maleimido methyl)cyclohexane-1-carboxylate, N-succinimidyl (4-iodine acetyl) aminobenzoate, N-succinimidyl 4-(1-maleimidophenyl) butyrate, iminothioran, S-acetyl mercaptosuccinic acid anhydride, methyl-3-(4'-dithiopyrydyl)propionimidate, methyl-4-mercaptobutylylimidate, methyl-3-mercapto propionimidate and N-succinimidyl-S-acetyl mercaptoacetate.

In the present invention, the optical interference unit may radiate the interference light as transmitted light, or it may radiate the interference light as reflected light. In the former case, the target detection apparatus can be made a reflecting type apparatus, whereas in the latter case, the target detection apparatus can be made a transmitting type apparatus.

(Target Detecting Substrate)

The optical interference unit is the target detection substrate of the present invention, and it has the detailed construction described above.

The target detection substrate of the present invention comprises the film-like material on a substrate, interferes with the irradiated light and can interact with the detection target. It interferes with the light radiated by the optical irradiation unit so as to radiate it as interference light, and after interacting with the detection target, the wavelength of the interference light can be changed.

The target detection substrate of the present invention may be used for detecting the detection target, but it may also be used in colorimetry, flame photometry, monochromators, lasers, optical communications and optical communications-related fields, and is particularly suitable for the target detection apparatus or target detection method of the present invention.

In this target detection substrate, the substrate surface is preferably subjected to one of hydrophilic treatment and lipophilic treatment. In this case, for example, if the substrate surface is given a hydrophilic treatment, the rod-shaped material such as an α-helix polypeptide is arranged standing on the substrate, whereas if the substrate surface is given a hydrophobic treatment, the rod-shaped material such as an α-helix polypeptide is arranged in rows on the substrate.

The hydrophilic treatment and lipophilic treatment are performed using, for example, a coupling agent.

<Wavelength Change Detecting Unit>

The wavelength change detecting unit is installed in a part of the interference light, and has the function of detecting a wavelength change of the interference light radiated by the optical interference unit.

The wavelength change detecting unit is not particularly limited provided that it has the function and may be suitably selected according to the purpose, but as examples, (1) only light of a specific wavelength is transmitted, and this light of specific wavelength is detected, and (2) the spectrum before wavelength change of the interference light, and the spectrum after wavelength change of the interference light are measured, and the differential spectrum is measured.

Among these, in the case of the (1), before the detection target interacts with the interference light, the wavelength change detecting unit transmits interference light, and after the detection target has interacted with the interference light, interference light of a specific, changed wavelength is transmitted. Alternatively, before the detection target interacts with the optical interference unit, interference light of a specific wavelength is transmitted, and after the detection target interacts with the optical interference unit, interference light of a changed wavelength is transmitted. In this way, if it is very difficult to detect a slight change, i.e., if there is only a slight wavelength change (wavelength shift) by simply measuring the ordinary spectral curve, this can be easily and reliably detected. As the wavelength detection unit detects the transmission of this interference light, the wavelength change of the interference light can be detected, and the interaction of the detection target with the optical interference unit, i.e., the presence of this detection target in the sample, can be detected easily, rapidly and with high sensitivity.

Further, from the magnitude of the transmitted light (transmitted light intensity), quantitative measurement of the detection target can be performed. Specifically, a calibration curve is first drawn showing the relation between the transmitted light amount of the interference light (transmitted light intensity) and the detection target capture amount due to the optical interference unit (target detection substrate). Hence, when the detection target content is measured for the sample containing the detection target, if the transmitted light amount of the interference light (transmitted light intensity) is measured, the detection target amount captured by the optical interference unit (target detection substrate) can be quantitatively measured from this calibration curve.

Alternatively, in the case of the (2), the spectral difference before and after the wavelength of the interference light has changed, i.e., the differential spectrum, is measured by the wavelength change detecting unit, so if a slight change is very difficult to measure by measuring only the ordinary spectral curve, i.e., when there is only a very small wavelength change (wavelength shift), this can be detected with ease and reliability, the wavelength change can be transformed into a spectral intensity, and this can be amplified as desired. As a result, even a very small wavelength change can be detected as an amplified spectral intensity, and can be detected with high sensitivity by a simple, rapid and highly sensitive detection.

Further, by measuring the spectral intensity, a quantitative measurement of the detection target can be performed. Specifically, a calibration curve is first drawn showing the relation between the transmitted light amount of the interference light (transmitted light intensity) and the wavelength intensity in the differential spectrum of the wavelength change (peak shift) of the interference light due to the optical interference unit (target detection substrate), or, a calibration curve is first drawn showing the relation between the wavelength intensity of the differential spectrum and the detection target amount captured by the optical interference unit (detection target substrate), and when the detection target content is measured for a sample containing the detection target, by measuring the wavelength intensity of the differential spectrum of the wavelength change (peak shift) of the interference light, the detection target amount captured by the interference unit (target detection substrate) can be quantitatively measured from this calibration curve.

A specific example of (1) is a combination of an interference filter with an optical detection sensor which can detect transmitted light which has passed through the interference filter. In this case, the interference filter transmits interference light before the detection target interacts with the interference light, and after the detection target has interacted with the interference light, interference light of a specific wavelength is transmitted. Alternatively, interference light of a specific wavelength is transmitted before the detection target interacts with the optical interference unit, and after the detection target interacts with the optical interference unit, interference light of a changed wavelength is transmitted. In this way, if it is very difficult to detect a slight change, i.e., if there is only a slight wavelength change (wavelength shift) by simply measuring the ordinary spectral curve, this can be easily and reliably detected. As the optical detection sensor detects the transmission of this interference light through the interference filter, the wavelength change of the interference light can be detected, and the interaction of the detection target with the optical interference unit, i.e., the presence of this detection target in the sample, can be detected. As a result, even if there is only a very slight wavelength change, the optical detection sensor can detect the transmitted interference light, and with high sensitivity. Also, whether the interference filter transmits interference light of a specific wavelength after the detection target interacts with the optical interference unit, or whether it transmits interference light of a specific wavelength before the detection target interacts with the optical interference unit, if the optical detection sensor measures the transmission amount of interference light, a quantitative measurement of the detection target can be performed.

The interference filter is not particularly limited and may be suitably selected according to the purpose, and commercial products may also be used.

The interference filter interferes only with incident light of a specific wavelength, and transmits incident light of wavelengths other than the specific wavelength.

The optical detection sensor is not particularly limited and may be suitably selected according to the purpose, examples being a CdS cell, photodiode, photoelectric tube, pyroelectric sensor, CCD sensor or PSD sensor.

Specific examples of (2) are spectrophotometers known in the art.

In the target detection apparatus according to the present invention, the optical irradiation unit irradiates light. The light interference unit interferes with the light irradiated by the irradiation unit, and radiates it as interference light. The optical interference unit can interact with the detection target, and after it has interacted with the detection target, it changes the wavelength of the interference light. The wavelength change detecting unit detects the wavelength change of the interference light radiated by the interference unit. Consequently, due to the wavelength change of the interference light detected by the wavelength change detecting unit, the interaction of the detection target with the optical interference unit, i.e., the presence of the detection target in the sample, can be detected.

The target detection apparatus of the present invention can be used in various fields, and can detect various targets such as pathogens, biological substances and toxic substances with efficiency, reliability and ease. Further, these measurements may be performed quantitatively, and can be conveniently used as a diagnostic apparatus, analysis apparatus or quantitative measurement apparatus.

(Target Detection Method)

The target detection method of the present invention comprises an optical irradiation step, a wavelength change detection step, and may comprise other steps if required.

The target detection method of the present invention may conveniently be applied to the target detection apparatus of the present invention and the target detection substrate of the present invention. If the target detection apparatus of the present invention is implemented, the target detection method of the present invention will be used.

The optical irradiation step is a step wherein light is irradiated to an optical interference unit (target detection substrate) which can interact with the detection target, and radiated as interference light.

As described above, the optical interference unit (target detection substrate) preferably has the function of changing the wavelength of interference light after interaction with the detection target.

To irradiate light to the optical interference unit (target detection substrate), the optical irradiation unit may conveniently be used.

When light is irradiated to the optical interference unit (target detection substrate), the optical interference unit can radiate the interference light by reflection or transmission.

The wavelength change detection step is a step which detects the wavelength change of the interference light.

To detect the wavelength change of the interference light, the wavelength change detecting unit may conveniently be used.

In the wavelength change detection step, the detection of the wavelength change of the interference light, insofar as it concerns the wavelength change detecting unit in the target detection apparatus, is as described above. For example, the wavelength change detecting unit transmits interference light before the detection target interacts with the interference light, and after the detection target has interacted with the interference light, interference light of a specific changed wavelength is transmitted. Alternatively, interference light of a specific wavelength is transmitted before the detection target interacts with the optical interference unit, and after the detection target interacts with the optical interference unit, interference light of a changed wavelength is transmitted. In this way, if it is very difficult to detect a slight change, i.e., if there is only a slight wavelength change (wavelength shift) by simply measuring the ordinary spectral curve, this can be easily and reliably detected. As the wavelength detecting unit detects the transmission of this interference light, the wavelength change of the interference light can be detected, and the interaction of the detection target with the optical interference unit, i.e., the presence of this detection target in the sample, can be detected easily, rapidly and with high sensitivity.

Further, from the magnitude of the transmitted light (transmitted light intensity), a quantitative measurement of the detection target can be performed. Specifically, a calibration curve is first drawn showing the relation between the transmitted light amount of the interference light (transmitted light intensity) and the detection target capture amount due to the optical interference unit (target detection substrate). Hence, when the detection target content is measured for the sample containing the detection target, if the transmitted light amount of the interference light (transmitted light intensity) is measured, the detection target amount captured by the optical interference unit (target detection substrate) can be quantitatively measured from this calibration curve.

Alternatively, for example, the spectral difference before and after the wavelength of the interference light has changed, i.e., the differential spectrum, is measured by the wavelength change detecting unit, so if a slight change is very difficult to measure by measuring only the ordinary spectral curve, i.e., when there is only a very small wavelength change (wavelength shift), this can be detected with ease and reliability, the wavelength change can be transformed into a spectral intensity, and this can be amplified as desired. As a result, even a very small wavelength change can be detected as an amplified spectral intensity, and can be detected with high sensitivity by a simple, rapid and highly sensitive detection.

Further, by measuring the spectral intensity, a quantitative measurement of the detection target can be performed. Specifically, a calibration curve is first drawn showing the relation between the transmitted light amount of interference light (transmitted light intensity) and the wavelength intensity in the differential spectrum of the wavelength change (peak shift) of the interference light due to the optical interference unit (target detection substrate), or, a calibration curve is first drawn showing the relation between the wavelength intensity of the differential spectrum and the detection target amount captured by the optical interference unit (detection target substrate), and when the detection target content is to be measured for a sample containing the detection target, by measuring the wavelength intensity of the differential spectrum of the wavelength change (peak shift) of the interference light, the detection target amount captured by the interference unit (target detection substrate) can be quantitatively measured from this calibration curve.

In the target detection method according to the present invention, in the optical irradiation step, light is irradiated to the optical irradiation unit (target detection substrate) which can interact with the detection target, and is radiated as interference light. In the wavelength change detecting step, the wavelength change of the interference light is detected. For this purpose, from the wavelength change of the interference light detected by the wavelength change detecting unit, the fact that the detection target has interacted with the optical interference unit (target detection substrate), i.e., the presence of the detection target in the sample, can be detected.

In the target detection method according to the present invention, when a target detection substrate is used as the optical interference unit, interference light with a sharp spectral curve can be radiated, and even if there is only a very slight wavelength change (wavelength shift) of the interference light, it can be simply, reliably and rapidly detected with high sensitivity, which is an advantage. The target detection method according to the present invention may be used in various fields, as it permits detection of various targets such as pathogens, biological substances and toxic substances with efficiency, reliability and ease. Further, these measurements may be performed quantitatively, and it can be conveniently used as a diagnostic method, analysis method or quantitative measurement method.

Hereafter, the present invention will be described by unit of examples, but it will be understood that the invention should not be construed as being limited thereby.

EXAMPLE 1

First, a monomolecular film of an α-helix polypeptide was formed on a substrate as the rod-shaped organic molecule, a laminated film (film-like material) was formed by laminating the same monomolecular film on this monomolecular film, and the relation between the number of laminated layers and the structural coloration was examined.

As the α-helix polypeptide, poly(n-hexyl L-glutamate (hereafter referred to as "PHeLG") was used comprising a monomer unit wherein the hydrogen atom of the carboxyl group of glutamic acid was replaced by a n-hexyl group. This PHelG was obtained by a polymerization reaction of L-glutamic acid-γ methyl ester using benzylamine as polymerization initiator. The polymerization degree as measured by $^1$H-NMR was 114. The substrate was a silicone substrate (Shin-Etsu Chemical Co., Ltd.) subjected to a surface treatment by octadecyl trimethoxysilane (Tokyo Chemical Industries). The monomolecular film was formed using a LB film-forming apparatus Japan Laser & Electronics Laboratory, NL-LB400 NK-MWC).

In addition, in PHeLG, the pitch of the spiral of the α-helix was 0.15 (nm/amino acid residue), and the diameter of the α-helix was 1.5 (nm).

For a laminated film (film-like material) comprising a laminate of 120 of these monomolecular film layers, when the FT-IR spectrum was measured, four peaks were obtained. One is a peak at 1738 $cm^{-1}$ due to the C=O group of the side chain. Another is a strong peak at 1656 cm$^{-1}$ due to an amide group I in the α-helix structure. Another is a small, weak peak at 1626 cm$^{-1}$ due to an amide group I in the beta-structure. The last one is a peak at 1551 cm$^{-1}$ due to an amide group II in the α-helix structure. From the measurement results of this FT-IR spectrum, it was confirmed that the above-mentioned PHeLG molecule maintains an α-helical structure in the monomolecular film.

Regarding the monomolecular film due to PHeLG, as the thickness when there were 20 monomolecular film layers due to this PHeLG was 32 nm, the thickness per layer was computed to be 1.6 nm.

Figure 6:
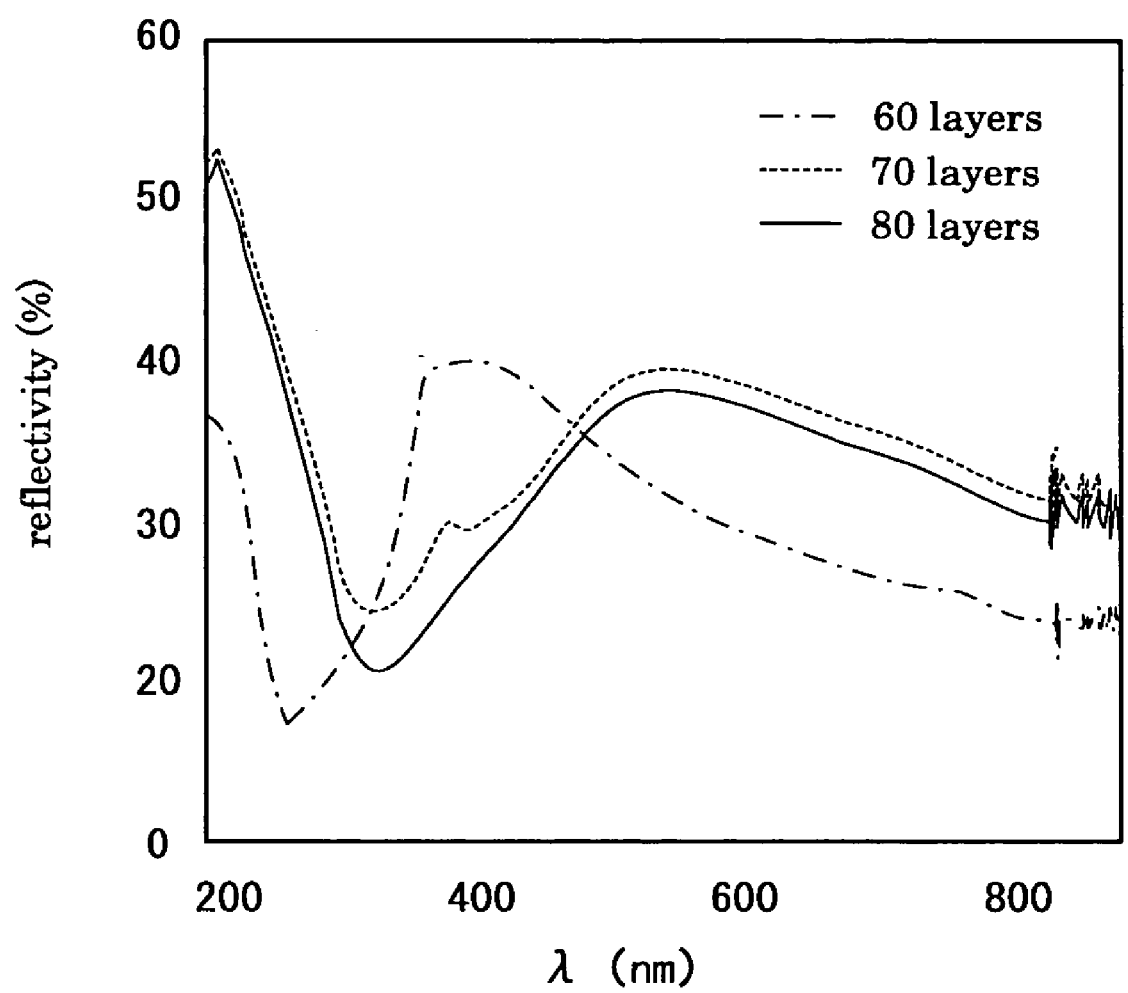
FIG. 6 is a graph showing the relation of the wavelength of structural color due to a laminated film (60 layers, 70 layers, 80 layers) of monomolecular films of rod-shaped organic molecules, and the thickness of this laminated film.

Next, when the relation between the number of laminated layers and structural coloration in the laminated film (film-like material) due to this monomolecular film was examined, it was found that when this laminated film contained 60 layers, 70 layers and 80 layers of these monomolecular films, the visible light reflection spectra shown in FIG. 6 were obtained. Also, a laminated film (film-like material) containing 40 to 50 layers of these monomolecular films showed a brown coloration, a laminated film (film-like material) containing 60 to 70 layers of these monomolecular films showed a dark blue (deep blue) coloration, a laminated film (film-like material) containing 80 to 100 layers of these monomolecular films showed a light blue (thin blue) coloration, a laminated film (film-like material) containing nearly 120 layers of these monomolecular films showed a yellow coloration, and a laminated film (film-like material) containing up to 120 layers of these monomolecular films showed a purplish red coloration.

Figure 7:
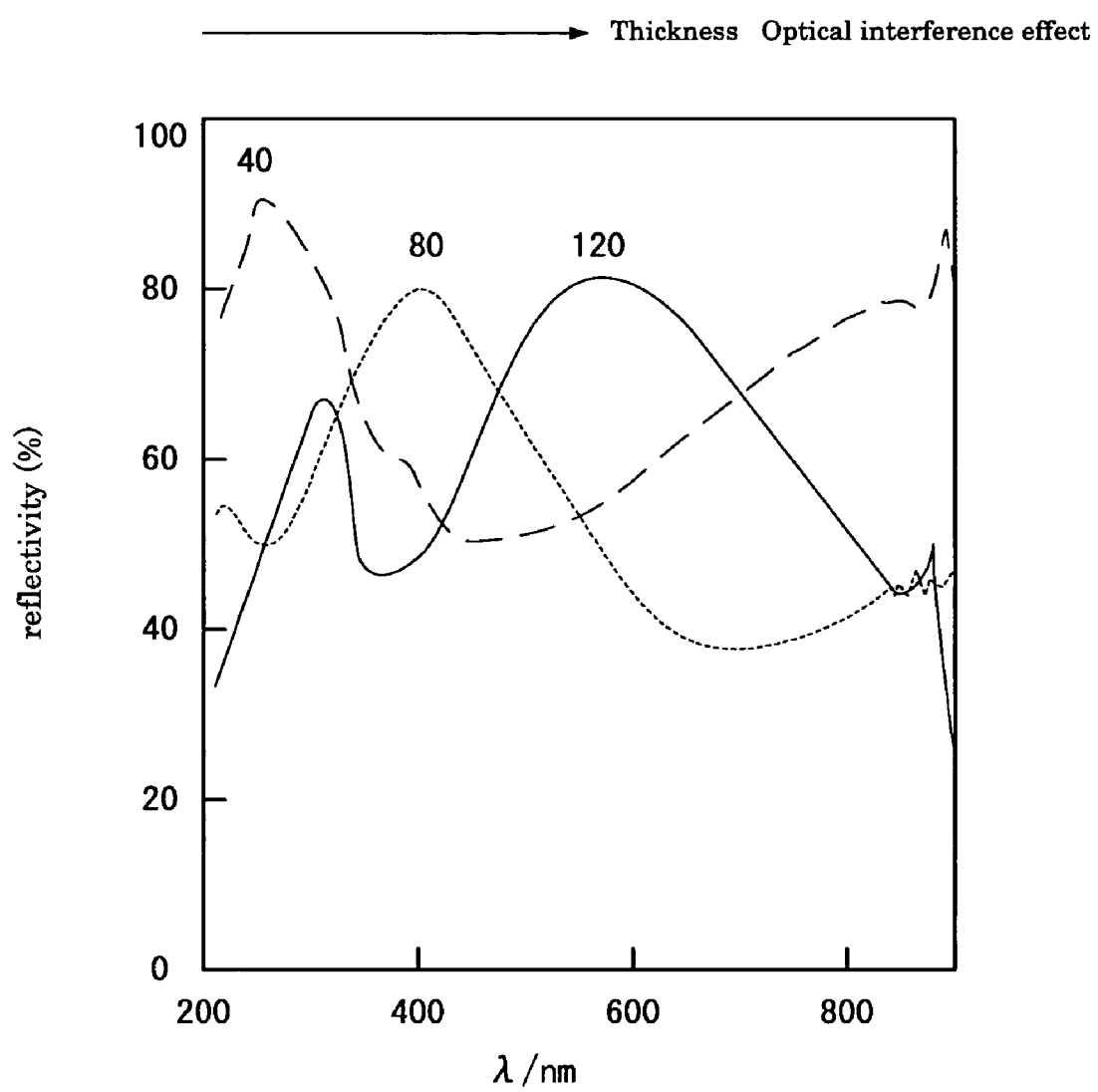
FIG. 7 is a graph showing the relation of the wavelength of structural color due to a laminated film (40 layers, 80 layers, 120 layers) of monomolecular films of rod-shaped organic molecules, and the thickness of this laminated film.

FIG. 7 shows the visible light reflection spectra for when the laminated film (film-like material) contained 40 layers of these monomolecular films, when the laminated film (film-like material) contained 80 layers, and when the laminated film (film-like material) contained 120 layers of these monomolecular films. The laminated film (film-like material) containing 80 layers showed a maximum reflectance (%) peak at 418 nm, and had a blue color. The laminated film (film-like material) containing 40 layers showed a minimum reflectance (%) at 456 nm, and had a brown (dark orange) color which is the complementary color to blue. On the other hand, the laminated film (film-like material) containing 120 layers showed a maximum reflectance (%) peak at 619 nm, a minimum reflectance (%) at 409 nm, and had a yellow color due to the light at 619 nm emphasized by the enfeebled light of wavelength 409 nm.

The wavelength (λ) of the visible light reflection spectrum is affected by the incidence angle (α) of the light on the laminated film (film-like material) due to the monomolecular film. The conditions under which this wavelength (λ) is emphasized are shown in the following (1), and the conditions under which this wavelength (λ) is enfeebled are as shown in the following (2):

$$\lambda = \frac{2tl}{m}\sqrt{n^2 - \sin^2\alpha} \quad (1)$$

$$\lambda = \frac{4tl}{2m-1}\sqrt{n^2 - \sin^2\alpha} \quad (2)$$

In the above-mentioned formula (1) and the above-mentioned formula (2), λ is the wavelength (nm) of the interference light, α is the incidence angle (°) of the light on the monomolecular film or the laminated film, t is the thickness (nm) of a monomolecular film, "l" is the number of monomolecular films, "n" is the refractive index of a monomolecular film, and "m" is an integer equal to 1 or more.

Figure 8:
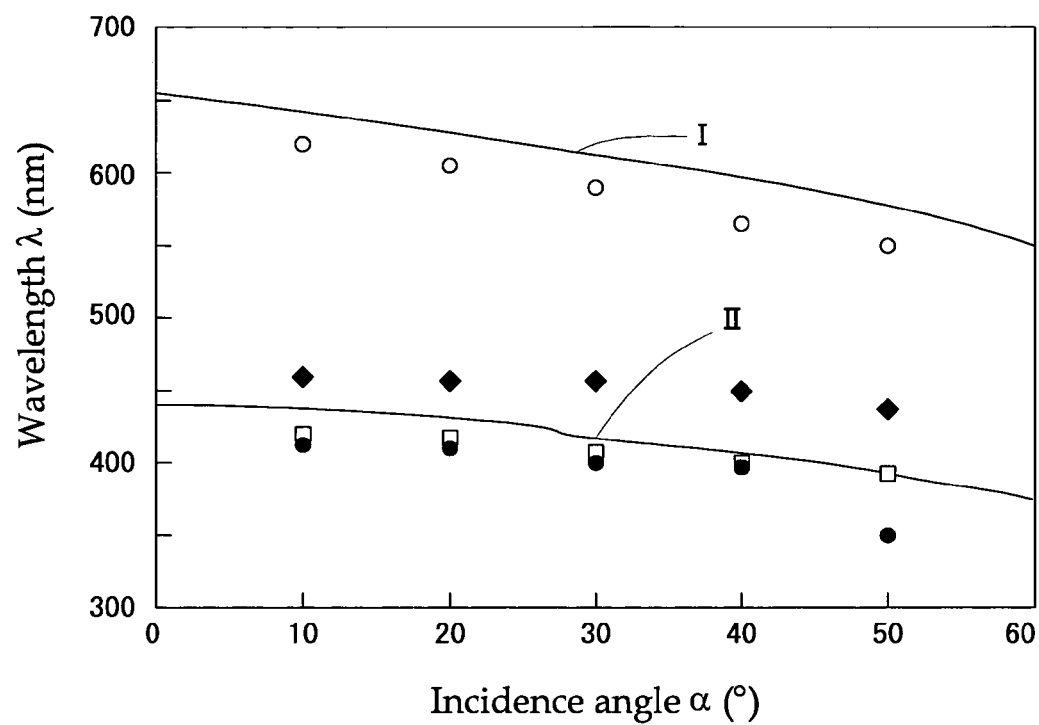
FIG. 8 is a graph showing the relation of a light incidence angle $\alpha(°)$ to the laminated film (40 layers, 80 layers, 120 layers) of monomolecular films of rod-shaped organic molecules, and a reflection wavelength $\lambda$(nm).

When the relation between the wavelengths (λ) of minimum and maximum intensity of the visible light reflection spectrums and the incidence angle (α) of the light on the laminated film (film-like material) of the monomolecular film was examined, as shown in FIG. 8, it was found that the measured values of the wavelength (λ) of the 5 reflection spectra for 5 incidence angles, effectively coincided with the wavelength (λs) computed by the formulae (1) and (2).

In FIG. 8, filled squares represent the wavelengths of minimum intensity in spectrums of the laminated film comprising 40 layers, open squares represent the wavelengths of maximum intensity in spectrums of the laminated film comprising 80 layers, open circles represent the wavelengths of maximum intensity in spectrums of the laminated film comprising 120 layers, and filled circles represent the wavelengths of minimum intensity in spectrums of the laminated film comprising 120 layers. The Line I was computed from Equation (1) for the conditions "l"=120 and "m"=1, and the Line II was computed from Equation (1) for the conditions "l"=80 and "m"=1, from Equation (2) for the conditions "l"=40 and "m"=1, or from Equation (2) for the conditions "l"=120 and "m"=2, respectively for the conditions "t"=1.7 (nm) and "n"=1.6 (the lines for these three calculation results effectively mutually overlap).

In this way, it was found that when light is irradiated to the film-like material having a specific thickness provided on the substrate, the interference light due to the film-like material has a wavelength in the visible spectrum and can be identified as an interference color.

Manufacture of Optical Interference Unit (Target Detecting Substrate)

Next, as the substrate on which the film-like material is arranged, a pre-colored substrate having an oxide film was manufactured as follows. An oxide film (SiO$_2$ film) $50a$ was formed on the surface of a silicon substrate by heat-treating the silicon substrate (Shin-Etsu Chemicals) at approximately 1000° C. for 3 hours. For this pre-colored substrate, its interference light (peak top is about 508 nm (thin line in FIG. 18)) is green, and it had a green color. The surface area of the silicon substrate is $3 \times 10^{14}$ nm$^2$ (15 mm×20 mm).

On the other hand, according to the following synthesis scheme, poly benzyl-L-glutamate having biotin at the end (PBLG$_{21}$-bio) was synthesized as the α-helix polypeptide which is the rod-shaped organic molecule. Specifically, poly benzyl-L-glutamate (PBLG$_{21}$-bio) having a polymerization degree of 21 was synthesized by carrying out a polymerization of the benzyl-L-glutamate derivative (BLG-NCA) synthesized by the synthesis scheme shown in Formula 1, using the biotin derivative shown in Formula 2 as a polymerization initiator.

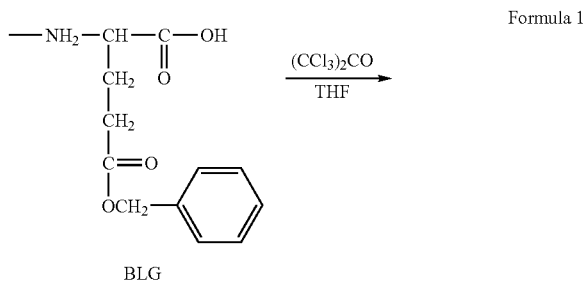

Formula 1

-continued

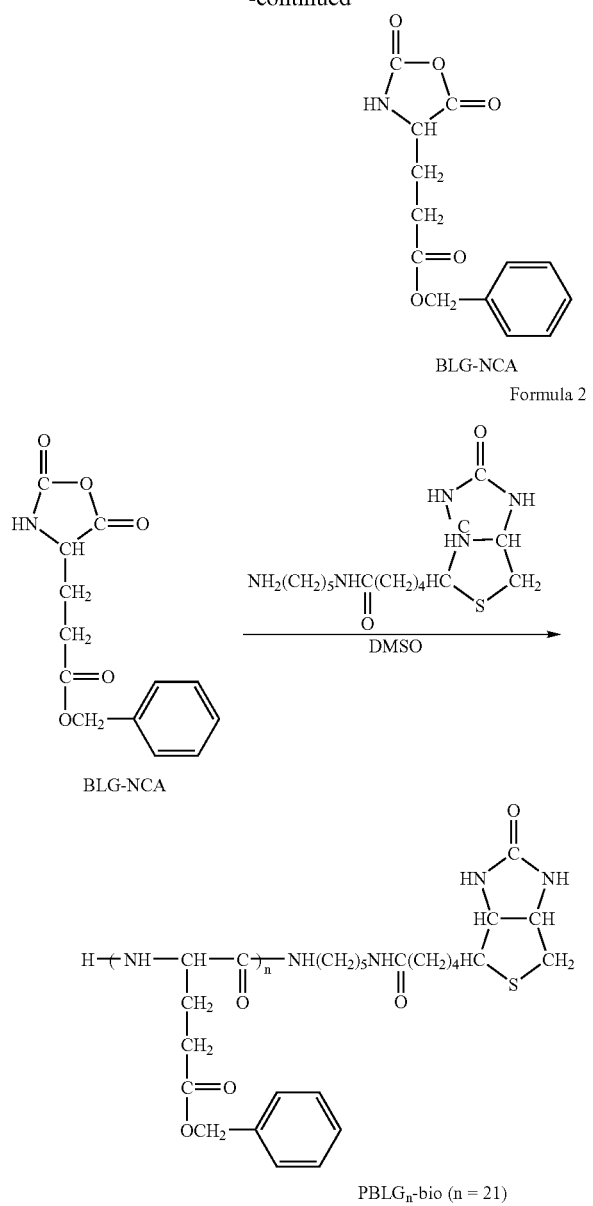

BLG-NCA

Formula 2

BLG-NCA

PBLG$_n$-bio (n = 21)

When the refractive index of this polybenzyl-L-glutamate (PBLG$_{21}$-bio) was measured using an Abbe's refractometer (Atago Co., Ltd.), it was about 1.5.

Figure 9:
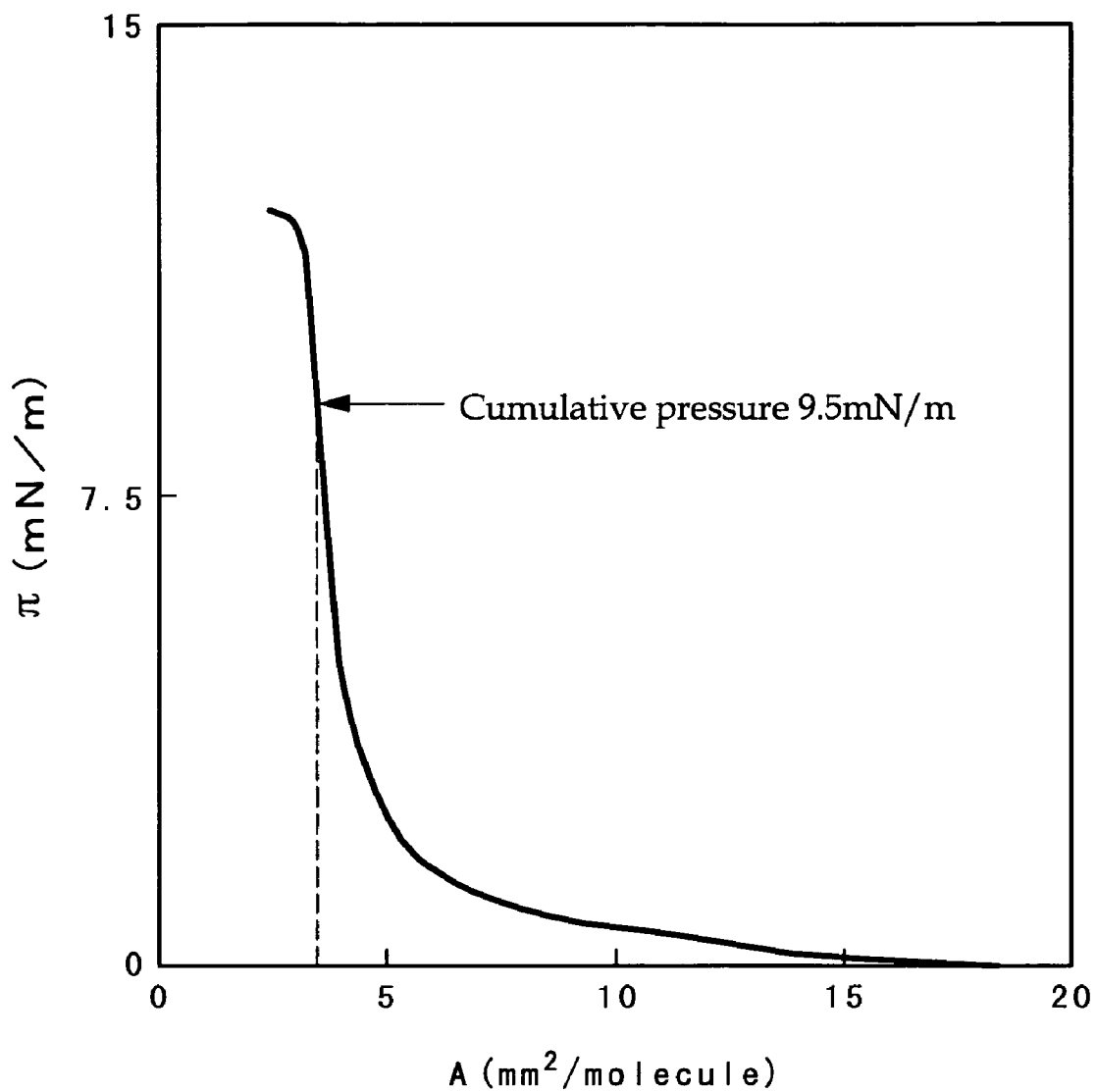
FIG. 9 is a graph showing a cumulative pressure when rod-shaped organic molecules 10 are stacked on a substrate 50 by the LB method.
Figure 10:
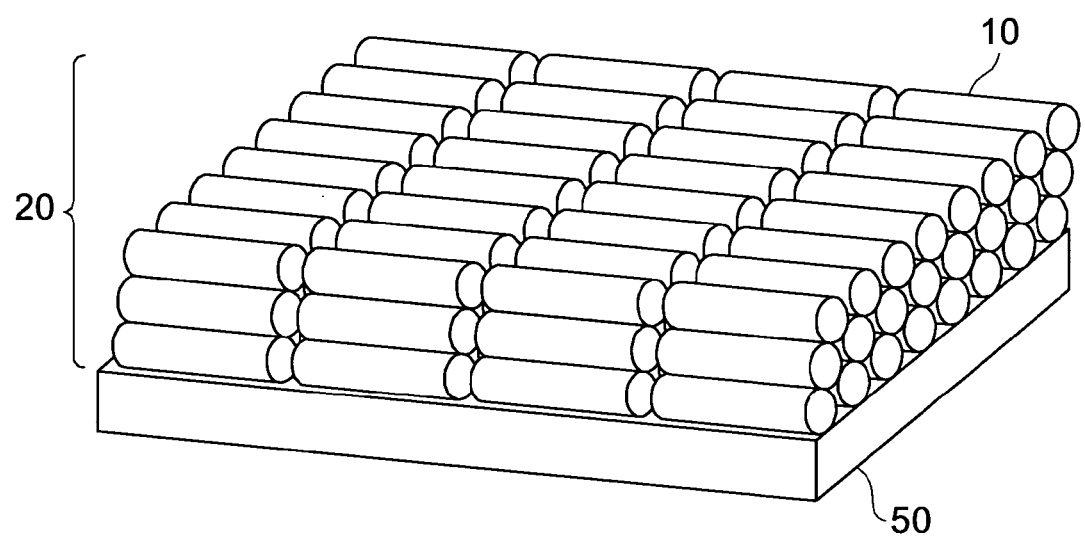
FIG. 10 is a schematic descriptive diagram showing one example of an optical interference unit (target detection substrate) of the present invention.

Ten layers of this synthetic polybenzyl-L-glutamate (PBLG$_{21}$-bio) were laminated on a substrate 50 (the pre-colored substrate) by the LB method at a cumulative pressure of 9.5 mN/m (FIG. 9: in FIG. 9, laminated at a cumulative pressure on the vertical axis of 9.5 mN/m). Specifically, a lamination layer film 20 (film thickness approx. 13.25 nm) comprising ten layers of the monomolecular (film thickness approx. 1.33 nm) having this polybenzyl-L-glutamate (PBLG$_{21}$-bio) as the rod-shaped organic molecule 10, was formed (FIG. 10: in FIG. 10, the lamination film does not show ten layers to simplify the illustration). The optical interference unit (target detecting substrate) thus obtained gives an interference light color (interference color, peak top approx. 545 nm (dotted line of FIG. 18)) which is yellowish, and it had a yellowish color.

Figure 11:
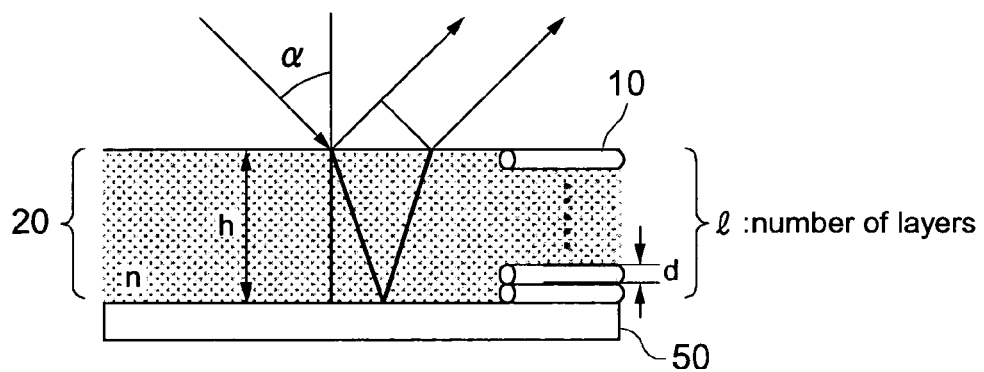
FIG. 11 is a schematic diagram for describing the light interference principle in the optical interference unit (target detection substrate) of the present invention.
Figure 12A:
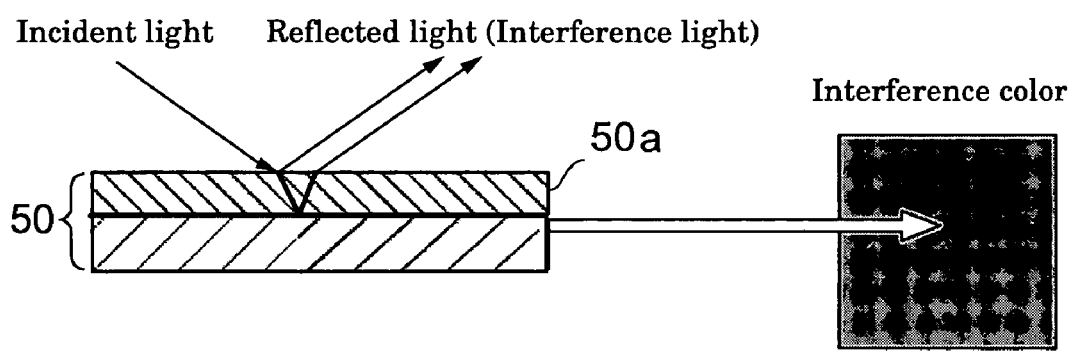
FIG. 12A is a schematic diagram for describing light interference and interference color of the substrate 50 when a film-like material 20 is not formed on the substrate 50.
Figure 12B:
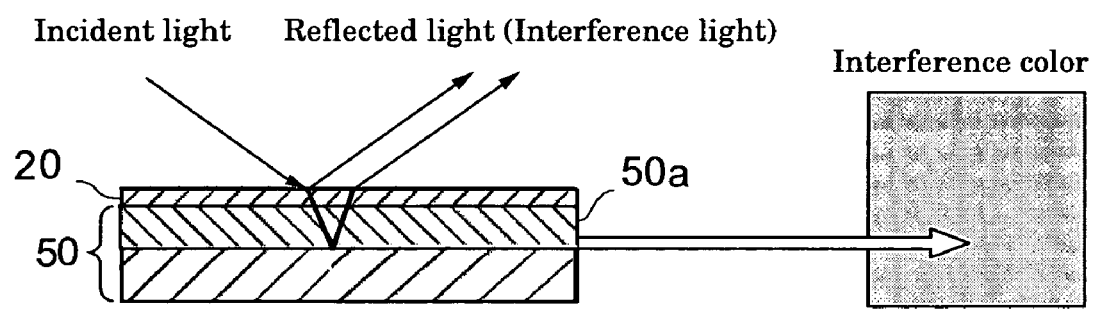
FIG. 12B is a schematic diagram for describing light interference and interference color in the optical interference unit (target detection substrate) of the present invention when the film-like material 20 is formed on the substrate 50.

The conditions under which this interference light is emphasized or enfeebled are as shown in the formulae of FIG. 11 wherein symbols and characters are as indicated in the upper drawing. FIG. 12A and FIG. 12B show the measurement of the interference light (interference color) in the pre-colored substrate (wherein the film-like material is not provided) (FIG. 12A), and the measurement of the interference light (interference color) in the optical interference unit (target detecting substrate) (FIG. 12B).

Interaction of Optical Interference Unit and Detection Target

Figure 13:
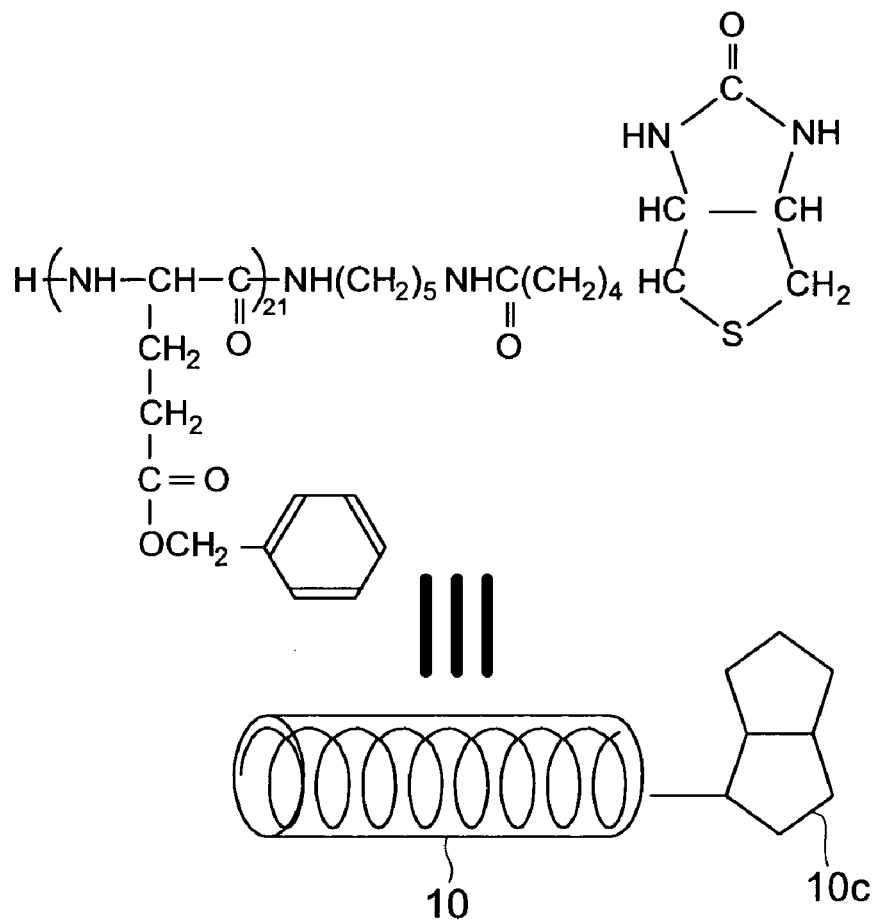
FIG. 13 is a schematic descriptive diagram for describing one aspect of the capture of a detection target by a target capturing body provided in the rod-shaped organic molecules.
Figure 13:
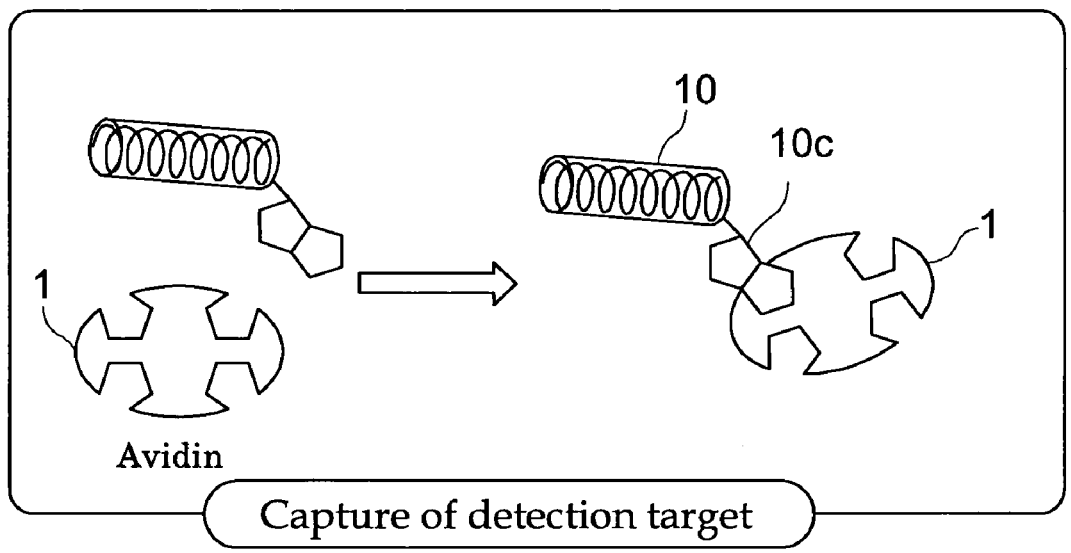
Figure 14:
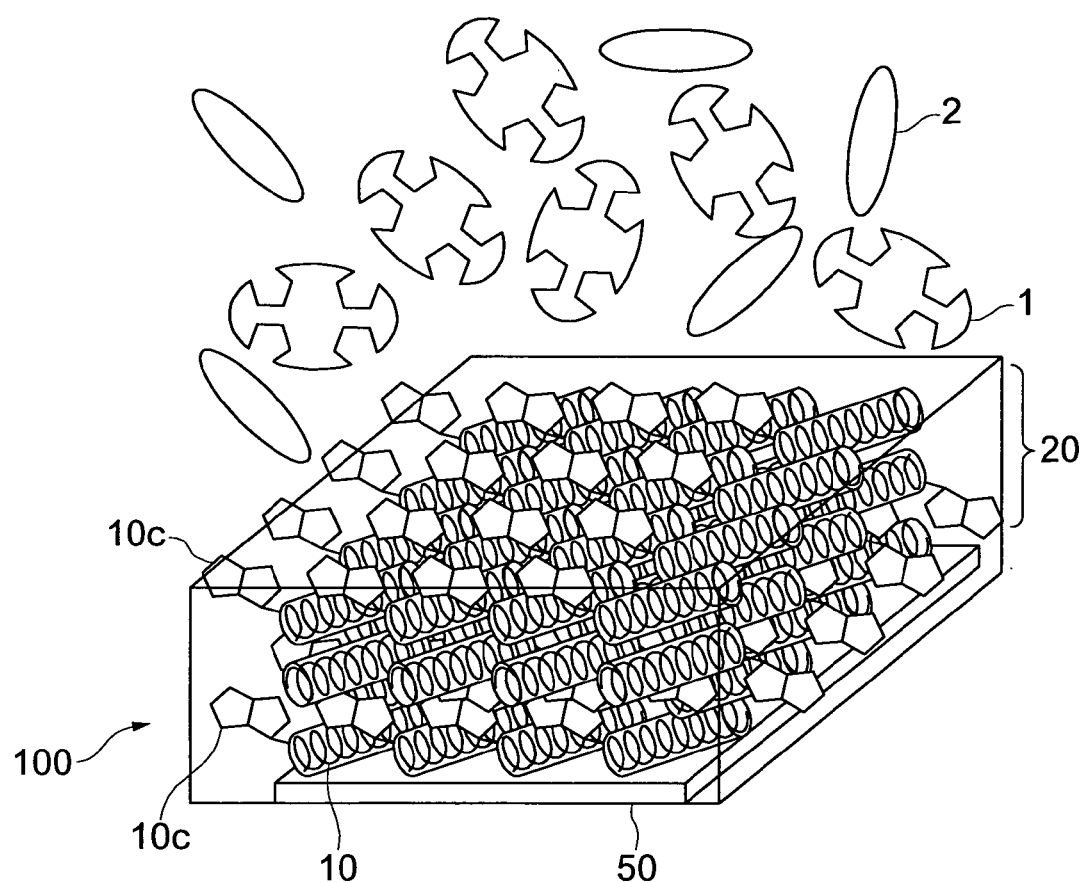
FIG. 14 is a schematic descriptive diagram showing an example of a situation wherein the optical detection unit (target detection substrate) of the present invention and a sample containing a detection target, were brought into contact.
Figure 15:
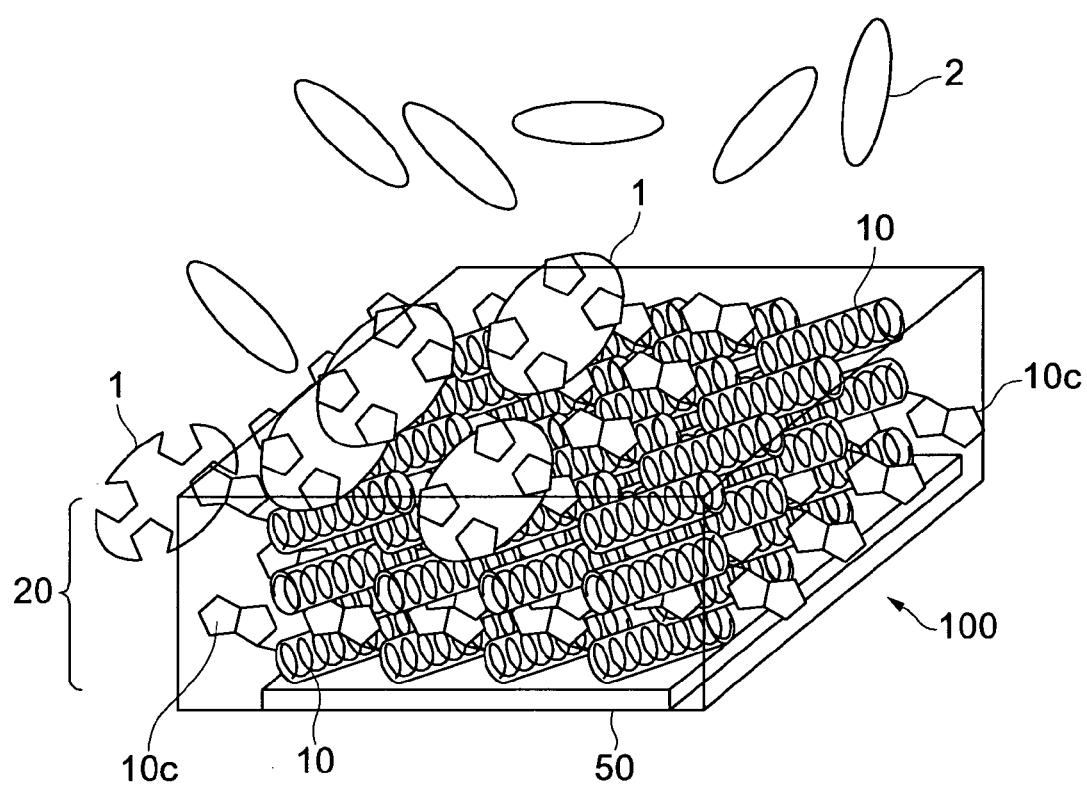
FIG. 15 is a schematic descriptive diagram showing an example of a situation wherein the detection target was captured by the target capturing body in the optical detection unit (target detection substrate) of the present invention.

The optical interference unit, i.e., the laminated film formed on the pre-colored substrate, was immersed in an aqueous solution ($1.1 \times 10^{-7}$M) of avidin as the detection target, and biotin as the target capturing body in the optical interference unit was made to interact (adsorption reaction) with avidin which was the detection target. The cross-sectional surface area of avidin was a little less than about 30 nm$^2$ (3 nm×3 nm×3.14). FIG. 13 is a schematic diagram of the interaction (adsorption reaction) of biotin 10c and avidin 1 in this example, FIG. 14 is a schematic diagram showing the state where the optical interference unit is immersed in the aqueous solution of avidin and non-target molecules 2, and FIG. 15 is a schematic diagram showing the interaction (adsorption reaction) of biotin in the optical detection unit with avidin in the aqueous solution of avidin. Subsequently, this optical detection unit was washed with pure water.

Wavelength Change Detection

Figure 16:
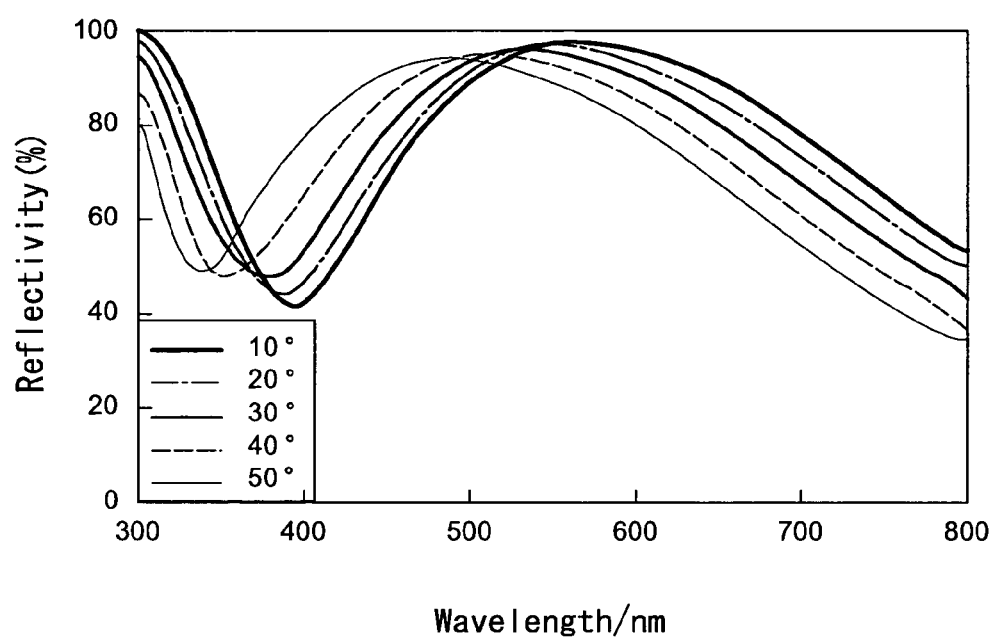
FIG. 16 is a graph of a spectrum showing incidence angle dependency of the intensity of the interference light due to the optical interference unit (target detection substrate) of the present invention.
Figure 17:
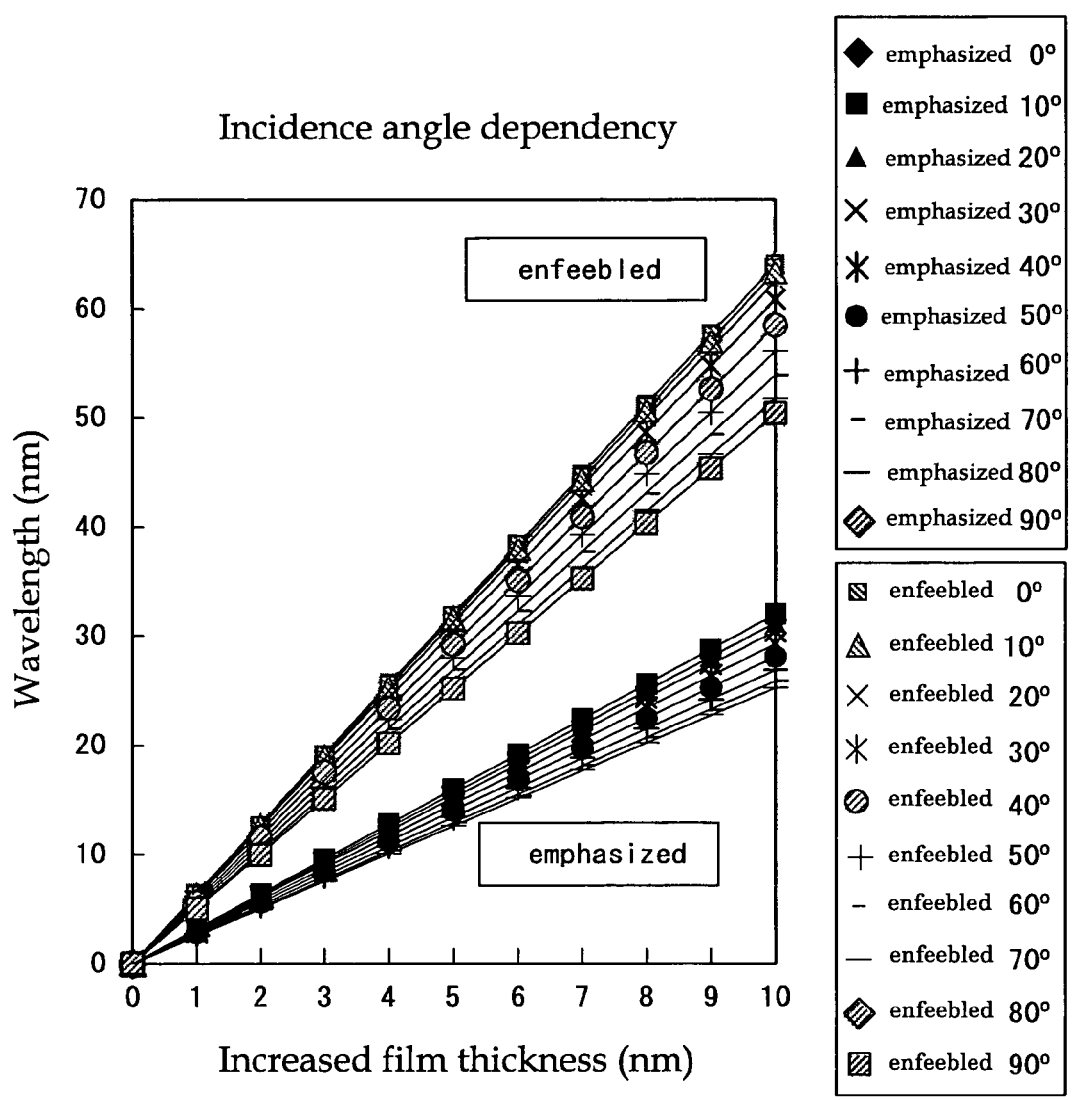
FIG. 17 is a graph showing the relation of interference light intensity to incidence angle and increased thickness of the optical interference unit (target detection substrate) of the present invention.

As the optical irradiation unit, a spectrophotometer (Jasco Corp., V560) was used as a light source. Light (xenon lamp light) was irradiated by this optical irradiation unit so that the incidence angle on the optical interference unit was 10°. The reason why the incidence angle was selected to be 10°, was that the incidence angle was selected from measurement data of the incidence angle dependence of the interference light in FIGS. 16 and 17.

Figure 18:
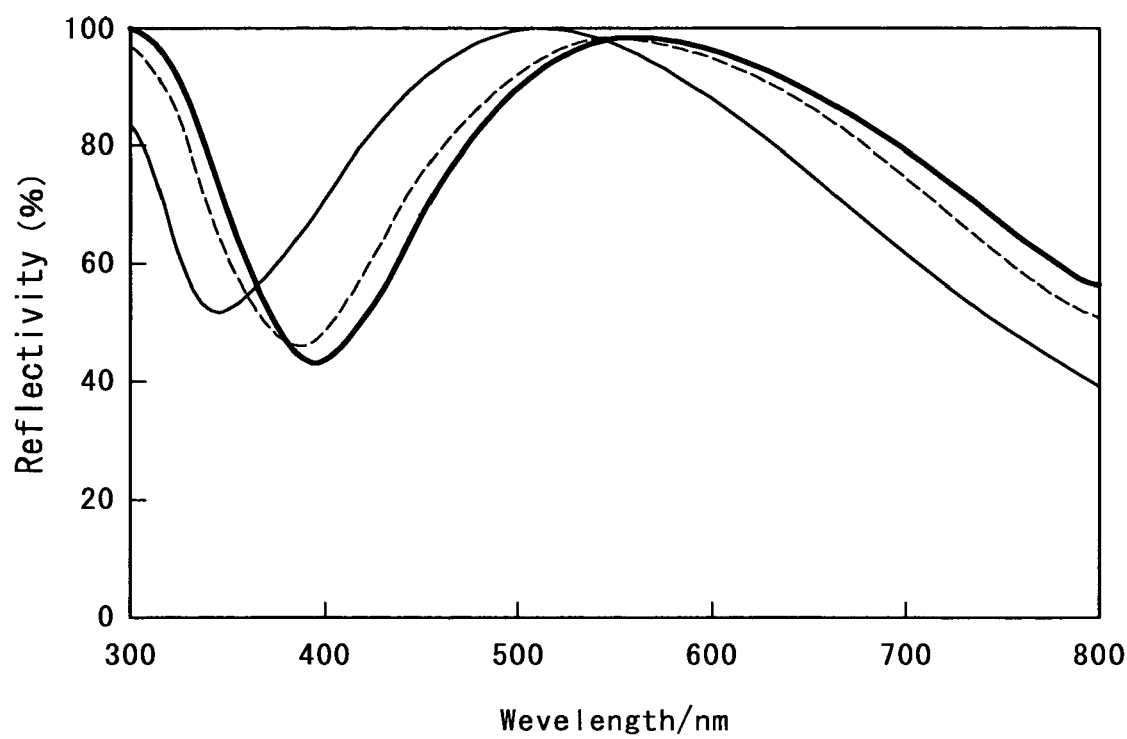
FIG. 18 is a graph showing the spectrum of interference light due to the substrate itself (solid line), the spectrum of interference light due to the optical interference unit (target detection substrate) of the present invention itself (dashed line), and the spectrum of interference light when this optical unit (target detection substrate) captures a detection target (bold line).

The spectrophotometer (Jasco Corp., V560) was disposed as a light-receiving unit in the path of the reflected light (interference light) due to the optical interference unit from the light irradiated by the optical irradiation unit. When the spectral wavelengths of this reflected light (interference light) were measured, the peak top was 565 nm (bold line in FIG. 18), and a peak shift of approximately 20 nm was observed compared to the situation before the interaction between the optical interference unit and detection target. If calculations are performed assuming a refractive index of 1.5, this corresponds to a film thickness variation of approximately 7.16 nm. This is confirmed to be due to adsorption of avidin having a diameter of approximately 6 nm on the surface of the optical interference unit. FIG. 18 shows these spectral measurement data.

<Calculation of Avidin Adsorption Amount>

The number of avidin adsorptions on the substrate can be computed from cross-sectional surface area of substrate/cross-sectional surface area of one avidin molecule, and was found to be $3 \times 10^{14}/3 \times 10^1 = 1 \times 10^{13}$ parts. Next, the number of absorption moles of avidin on this substrate can be computed from this number of adsorptions/Avogadro's number, and was found to be $1 \times 10^{13}/6 \times 10^{23} = 17 \times 10^{-12}$ M=17 pM.

Therefore, it was found that the avidin adsorption amount for a wavelength shift in the interference light of 20 nm is 17 pM(s).

Further, when the surface area of the substrate was approximately 5 mm$^2$, the wavelength shift (peak top shift)

of the interference light for an avidin adsorption amount of 1.4 pM, was of the order of 20 nm. Converting this to a weight of avidin, and assuming that the molecular weight of avidin is approximately 68,000, we obtain $1.4\times10^{-12}$ M×68,000=$9.5\times10^{-8}$ g (95 ng), which corresponds to an adsorption amount of 4.8 ng for a peak shift (wavelength shift) of 1 nm.

<Detection of Wavelength Change by Differential Spectrum Measurement and Quantitative Measurement of Detection Target>

Figure 19:
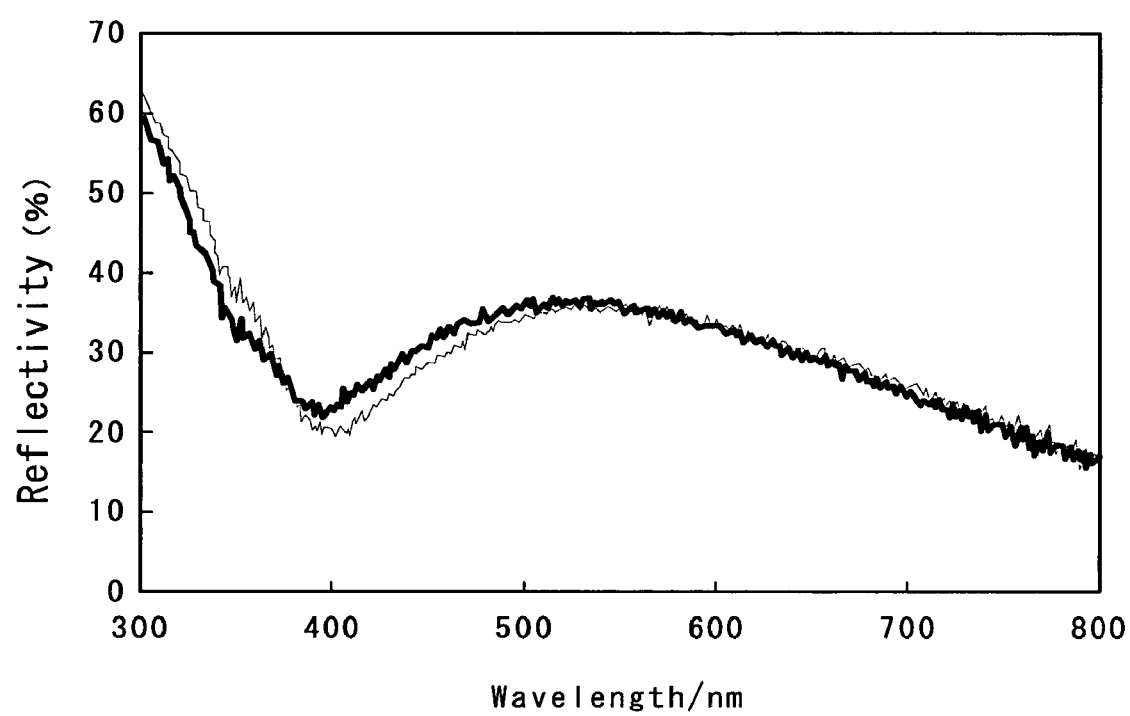
FIG. 19 is a graph showing the spectrum of the interference light due to the optical interference unit (target detection substrate) of the present invention, and the spectrum of interference light when the detection target (avidin) is captured.
Figure 20:
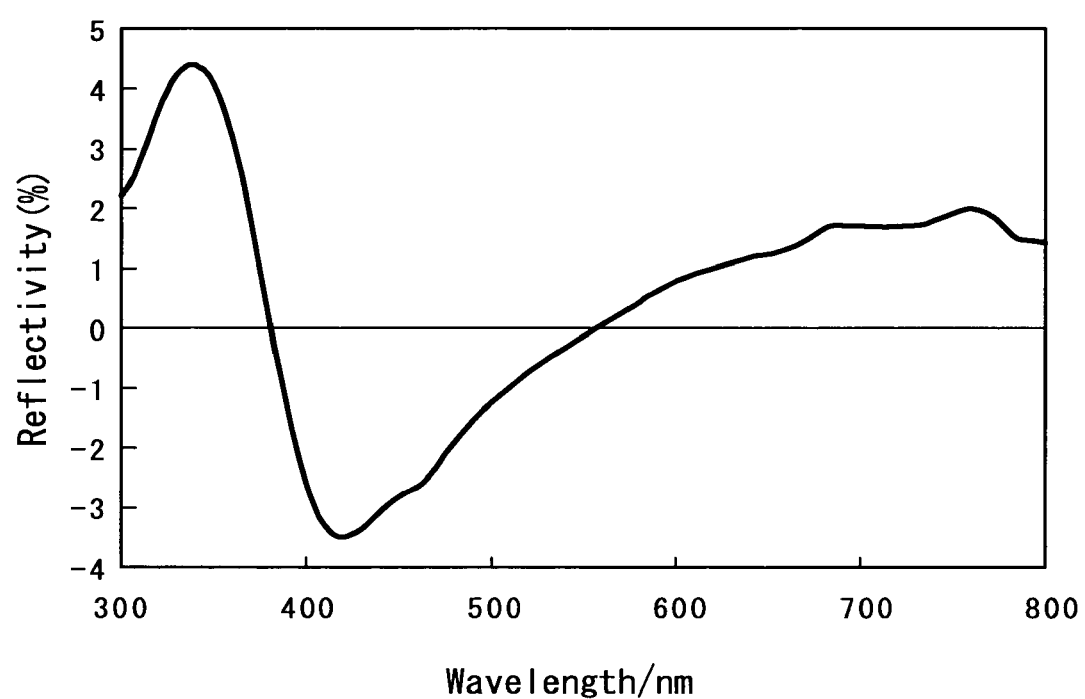
FIG. 20 is a graph showing a differential spectrum when the difference of the two spectral data shown in FIG. 19, is displayed.

The spectrum (bold line in FIG. 19) of the interference light due to the optical interference unit (target detecting substrate) and the spectrum (thin line in FIG. 19) of the interference light when the detection target (avidin) was captured, were measured. This result is shown in FIG. 19. As is clear also from the spectral data of FIG. 19, the two spectral curves almost coincide with each other, and it is difficult to detect the wavelength shift of the interference light from this spectral curve data. However, if the differential spectrum of the two spectral data is taken using the spectrophotometer, the result is as shown in FIG. 20, and the wavelength difference of the two spectra which was very difficult to detect in FIG. 19, appears as a large wavelength difference. Therefore, by detecting the differential spectrum, the wavelength difference of the interference light can be detected without measurement error, and with simplicity, rapidity and high sensitivity. This differential spectrum is obtained as a spectral intensity, and may therefore be amplified as desired by the spectrophotometer. In other words, even if the spectral intensity is very small, it can be detected with high sensitivity by amplification.

If the procedure below is followed, by measuring the spectral intensity, a quantitative measurement of the detection target can be performed. Specifically, a calibration curve is drawn showing the relation between the transmitted light amount of the interference light (transmitted light intensity), and the wavelength intensity in the differential spectrum of the wavelength variation (peak shift) of the interference light due to the optical interference unit (detection target substrate). Alternatively, a calibration curve is drawn showing the relation between the wavelength intensity of the differential spectrum, and the amount of the detection target captured by the optical interference unit (detection target substrate). When the detection target content is measured for a sample containing this detection target, if the wavelength intensity of the differential spectrum of the wavelength variation (peak shift) of the interference light is measured, the amount of the detection target captured by the optical interference unit (target detection substrate) can be quantitatively measured from this calibration curve.

Next, in the optical interference unit (target detection substrate) an identical procedure was followed except that the silicon substrate was replaced by an interference filter and the film-like material was replaced by a laminate of 88 layers of the rod-shaped organic molecules 10.

Figure 21:
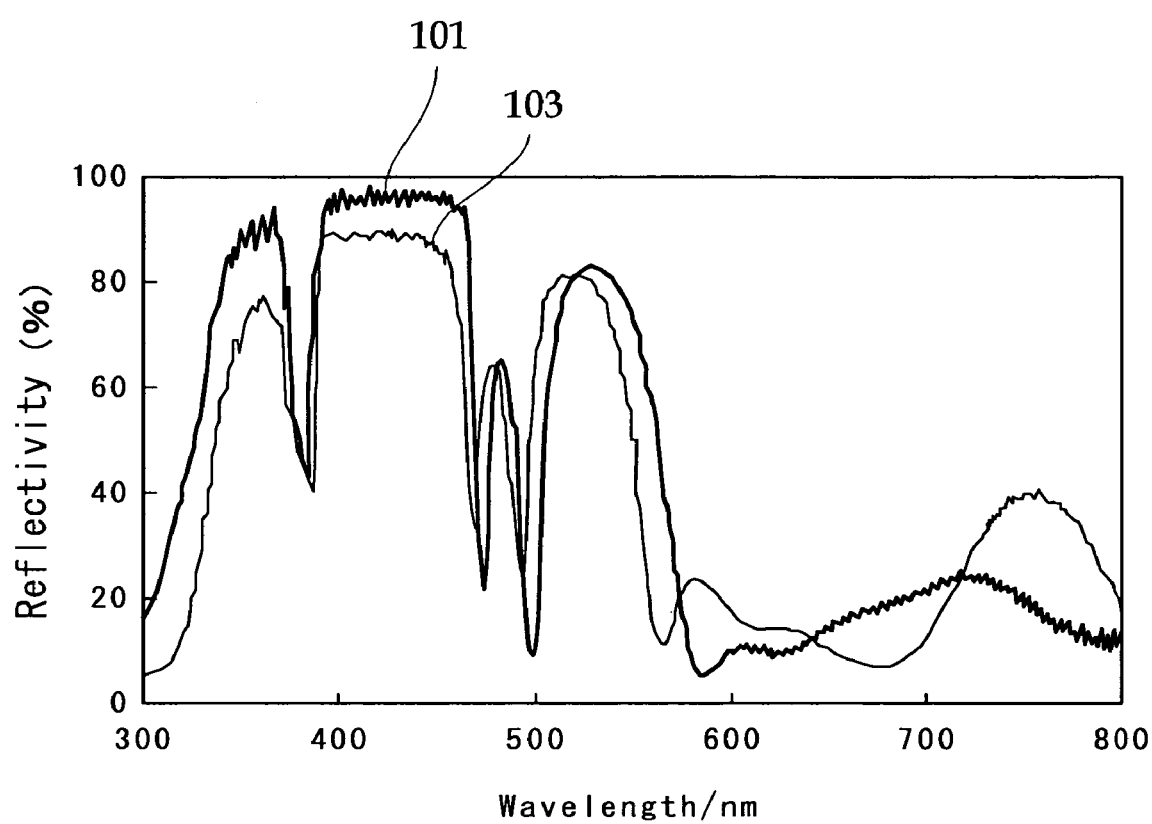
FIG. 21 is a graph showing the spectrum of interference light due to an interference filter, and the spectrum of interference light due to an interference unit (target detection substrate) formed from this interference filter as a substrate, and a film-like material wherein 88 layers of rod-shaped organic molecules are laminated on the surface thereof.
Figure 22:
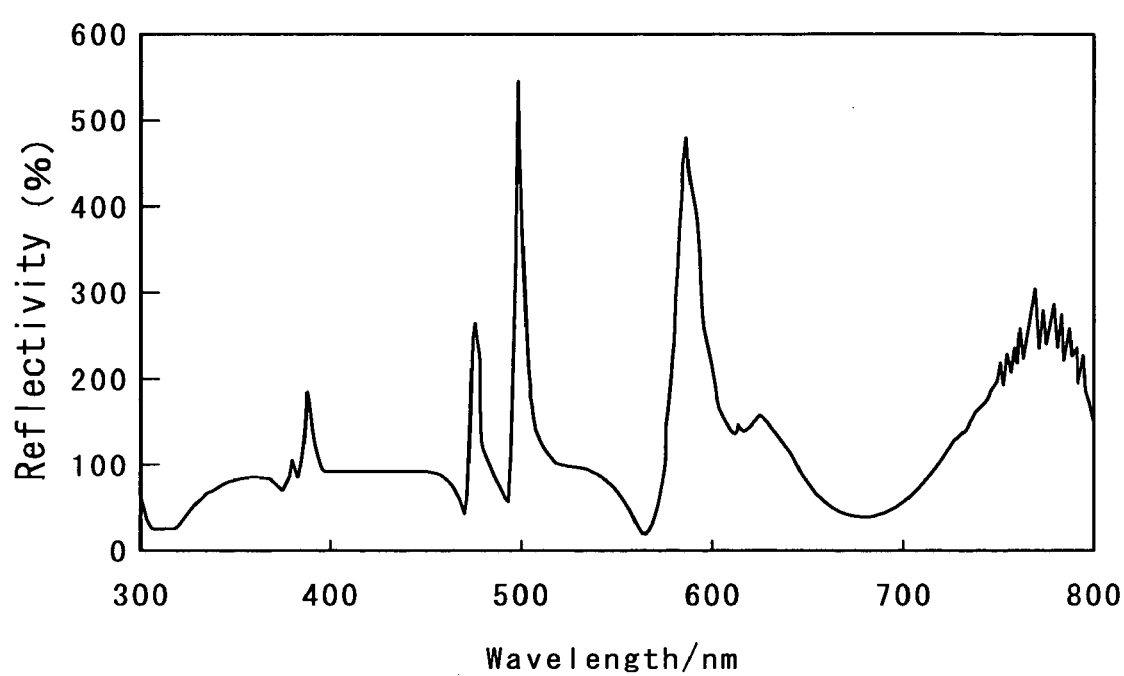
FIG. 22 is a graph showing a differential spectrum when the difference of the two spectra in FIG. 21, is displayed.

Herein, the interference light spectrum due to the interference filter itself 101 (bold line in FIG. 21) and the interference light spectrum due to an interference filter provided with the film-like material 103 (thin line in FIG. 21), were measured, as shown in FIG. 21. As is clear from the spectral data of FIG. 21, the two spectral curves resemble each other, and it is difficult to detect the wavelength shift (peak shift) of the interference light from this spectral curve data. However, if the differential spectrum of the two spectral data is taken by the spectrophotometer, the result is as shown in FIG. 22, and the wavelength difference of the two spectra which was very difficult to detect in FIG. 21, now appears as a large wavelength difference. Therefore, by detecting this differential spectrum, the wavelength difference of the interference light can be detected without measurement error, and with simplicity, rapidity and high sensitivity. This differential spectrum is obtained as a spectral intensity, and may therefore be amplified as desired by the spectrophotometer. In other words, even if the spectral intensity is very small, it may be detected with high sensitivity by amplification. Therefore, even if the silicon substrate is replaced by the interference filter, by measuring the differential spectrum in an identical way to the case where a silicon substrate is used, high sensitivity detection of the detection target is possible. In this case also, a quantitative measurement of the detection target can be performed as described above.

According to the present invention, the problems inherent in the prior art are resolved, and various detection targets such as pathogens, physiological substances and toxic substances can be detected with a reduced measurement error, together with high efficiency, simplicity, rapidity and high sensitivity, without using a costly measurement apparatus. Further, it also provides a target detection apparatus and target detection method capable of quantitative measurement, and a target detection substrate which can conveniently be used in this apparatus and method.

What is claimed is:

1. A target detection apparatus comprising:
    an optical irradiation unit which irradiates light,
    an optical interference unit comprising helical organic molecules each having a target capturing body bonded thereto, said helical organic molecules being aligned to form a film-like material, said film-like material having a refractive index, wherein said optical interference unit is capable of: interacting with a detection target, interfering with the light irradiated from the optical irradiation unit, radiating said light as interference light, and varying the wavelength of the interference light after interaction with the detection target, and
    a wavelength change detecting unit placed in the path of the interference light which detects the wavelength variation of the interference light radiated by the optical interference unit,
    wherein the optical interference unit further comprises a substrate, the film-like material being provided on the substrate, and the substrate comprising on a surface thereof an identical refractive index film having a refractive index that is substantially the same as the refractive index of the film-like material.

2. The target detection apparatus according to claim 1, wherein the wavelength change detecting unit transmits light of a specific wavelength, and can detect that light of the specific wavelength has been passed through.

3. The target detection apparatus according to claim 2, wherein the wavelength change detecting unit comprises an interference filter, and an optical detection sensor which can detect light which has passed through the interference filter.

4. The target detection apparatus according to claim 1, wherein the wavelength change detecting unit measures a spectrum before wavelength change of the interference light and a spectrum after wavelength change of the interference light, and can measure their differential spectrum.

5. The target detection apparatus according to claim 4, wherein the wavelength change detecting unit transforms the differential spectrum into a spectral intensity, and can amplify the spectral intensity.

6. The target detection apparatus according to claim 4, wherein the wavelength change detecting unit is a spectrophotometer.

7. The target detection apparatus according to claim 1, wherein the optical interference unit radiates interference light as at least one selected from a reflected light and a transmitted light.

8. The target detection apparatus according to claim 1, wherein each of the helical organic molecules is rod-shaped.

9. The target detection apparatus according to claim 8, wherein the film-like material is formed by a coating method.

10. The target detection apparatus according to claim 1, wherein the substrate is formed from at least one of semiconductor, ceramics, metal, glass, and plastics.

11. The target detection apparatus according to claim 1, wherein the substrate further comprises on a surface thereof a different refractive index film having a refractive index that is different from the refractive index of the film-like material.

12. The target detection apparatus according to claim 11, wherein the refractive index of the different refractive index film is different from a refractive index of the substrate.

13. The target detection apparatus according to claim 11, comprising a plurality of different refractive index films, refractive indices of the plurality of different refractive index films being mutually different.

14. The target detection apparatus according to claim 11, wherein the different refractive index film is a dielectric film.

15. The target detection apparatus according to claim 1, wherein the substrate is an interference filter.

16. The target detection apparatus according to claim 1, wherein at least a second film is formed on the surface of said film-like material.

17. The target detection apparatus according to claim 16, wherein said second film has a refractive index substantially the same as the refractive index of the substrate surface in contact with the film-like material.

18. The target detection apparatus according to claim 1, wherein the thickness of the film-like material is from 50 nm to 1 μm.

19. The target detection apparatus according to claim 1, wherein the film-like material is one of a monomolecular layer and a laminated film of the monomolecular layer.

20. The target detection apparatus according to claim 1, wherein the helical organic molecules are alpha-helix polypeptides.

21. The target detection apparatus according to claim 1, wherein the target capturing body is capable of interacting with the detection target by at least one selected from physical adsorption and chemical adsorption.

22. The target detection apparatus according to claim 21, wherein the detection target is avidin, and the target capturing body is biotin.

23. The target detection apparatus according to claim 1, wherein the target capturing body is at least one selected from enzyme, coenzyme, enzyme substrate, enzyme inhibitor, a clathrate compound, metal, antibody, antigen, protein, microorganism, virus, cell debris, metabolic product, nucleic acid, hormone, hormone receptor, lectin, sugar, physiologically active substance and physiologically active substance-receptor.

24. The target detection apparatus according to claim 23, wherein:

the clathrate compound is further selected from a monomolecular host compound, a polymolecular host compound, a polymer host compound, and an inorganic host compound;

the monomolecular host compound is further selected from cyclodextrin, a crown compound, cyclophane, azacyclophane, calixarene, cyclotriveratrylene, spherand, cavitand and, cyclic oligopeptide;

the polymolecular host compound is further selected from urea, thiourea, deoxycholic acid, perhydrotriphenylene, and tri-o-thymotide;

the polymer host compound is further selected from cellulose, starch, chitin, chitosan, and polyvinyl alcohol; and the inorganic host compound is further selected from an interlayer compound, zeolite, and a Hofmann complex.

25. The target detection apparatus according to claim 1, wherein the optical irradiation unit can irradiate a pencil light beam.

26. The target detection apparatus according to claim 1, wherein the optical irradiation unit is a laser irradiation device.

27. A target detection substrate comprising:

an optical interference unit comprising helical organic molecules each having a target capturing body bonded thereto, said helical organic molecules being aligned to form a film-like material, said film-like material having a refractive index; and a substrate, wherein the film-like material is provided on the substrate, and the target detection substrate is capable of interacting with a detection target, interfering with irradiated light and radiating the light as interference light, and changing the wavelength of the interference light after interacting with the detection target, and the substrate comprises on a surface thereof an identical refractive index film having a refractive index that is substantially the same as the refractive index of the film-like material.

28. The target detection substrate according to claim 27, wherein the interaction is at least one selected from physical adsorption and chemical adsorption.

29. The target detection substrate according to claim 27, wherein the interference light is radiated as at least one of reflected light and transmitted light.

30. The target detection substrate according to claim 27, wherein each of the helical organic molecules is rod-shaped.

31. The target detection substrate according to claim 27, wherein the substrate is formed from at least one of semiconductor, ceramics, metal, glass, and plastics.

32. The target detection substrate according to claim 27, wherein the substrate further comprises on a surface thereof a different refractive index film having a refractive index that is different from the refractive index of the film-like material.

33. The target detection substrate according to claim 32, wherein the refractive index of the different refractive index film is different from a refractive index of the substrate.

34. The target detection substrate according to claim 32, comprising a plurality of different refractive index films, refractive indices of the plurality of different refractive index films being mutually different.

35. The target detection substrate according to claim 32, wherein the different refractive index film is a dielectric film.

36. The target detection substrate according to claim 27, wherein the substrate is an interference filter.

37. The target detection substrate according to claim 27, wherein at least one dielectric film is further formed on the surface of the film-like material.

38. The target detection substrate according to claim 27, wherein the thickness of the film-like material is from 50 nm to 1 μm.

39. The target detection substrate according to claim 27, wherein the film-like material is one of a monomolecular layer and a laminated film of the monomolecular layer.

40. The target detection substrate according to claim 27, wherein the helical organic molecules are alpha-helix polypeptides.

41. A target detection method comprising the steps of:
(a) irradiating light to an optical interference unit that is capable of interacting with a detection target, and radiating the light as interference light;
said optical interference unit comprising helical organic molecules each having a target capturing body bonded thereto, and said helical organic molecules being aligned to form a film-like material, said film-like material having a refractive index,
wherein said optical interference unit further comprises a substrate, the film-like material being provided on the substrate, and the substrate comprising on a surface thereof an identical refractive index film having a refractive index that is substantially the same as the refractive index of the film-like material,
(b) detecting a wavelength change of the interference light upon capture of said detection target by said optical interference unit, and
c) generating a signal for display.

42. The target detection method according to claim 41, wherein the optical interference unit can change the wavelength of the interference light after interaction with the detection target.

43. The target detection method according to claim 41, wherein said optical interference unit is capable of: interacting with a detection target, interfering with irradiated light and radiating the light as interference light, and changing the wavelength of the interference light after interaction with the detection target.

* * * * *